United States Patent
Labow et al.

(10) Patent No.: US 7,374,911 B2
(45) Date of Patent: May 20, 2008

(54) INTERLEUKIN-1 RELATED GENE AND PROTEIN

(76) Inventors: Mark A. Labow, 422 Kimball Ave., Westfield, NJ (US) 07090; Vadim Iourgenko, 3002 Vroom Dr., Bridgewater, NJ (US) 08807

( * ) Notice: Subject to any disclaimer, the term of this patent is extended or adjusted under 35 U.S.C. 154(b) by 462 days.

(21) Appl. No.: 10/451,315

(22) PCT Filed: Dec. 20, 2001

(86) PCT No.: PCT/EP01/15125

§ 371 (c)(1),
(2), (4) Date: Jul. 10, 2003

(87) PCT Pub. No.: WO02/50113

PCT Pub. Date: Jun. 27, 2002

(65) Prior Publication Data

US 2004/0241807 A1    Dec. 2, 2004

Related U.S. Application Data

(60) Provisional application No. 60/257,509, filed on Dec. 21, 2000.

(51) Int. Cl.
*C12N 15/09* (2006.01)
*C12N 15/12* (2006.01)
*C07K 14/00* (2006.01)

(52) U.S. Cl. ............... 435/69.52; 435/69.1; 435/320.1; 435/325; 435/471; 536/23.5; 530/351

(58) Field of Classification Search ............ None
See application file for complete search history.

(56) References Cited

U.S. PATENT DOCUMENTS 6,339,141 B1 * 1/2002 Ballinger et al. ........... 530/351

FOREIGN PATENT DOCUMENTS

| WO | WO 00/71719 | 11/2000 |
| WO | WO 01/42304 | 6/2001 |
| WO | WO 01/55211 A2 | 8/2001 |

OTHER PUBLICATIONS

Kumar et al., "Identification and Initial Characterization of Four Novel Members of the Interleukin-1 Family", *J. Biol. Chem.*, vol. 275, No. 14, pp. 10308-10314 (2000).
Smith et al., "Four New Members Expand the Interleukin-1 Superfamily", *J. Biol. Chem.*, vol. 275, No. 2, pp. 119-1175 (2000).
The Sanger Centre and The Washington University Genome Sequencing Center, "Toward a Complete Human Genome Sequence", Genome Research, Cold Spring Harbor Laboratory Press, vol. 8, No. 11, pp. 1097-1108 (1998).

* cited by examiner

*Primary Examiner*—Eileen O'Hara
*Assistant Examiner*—Fozia Hamud
(74) *Attorney, Agent, or Firm*—Novartis Pharmaceuticals

(57) ABSTRACT

Disclosed in an interleukin-1 related gene and gene product. In particular, the invention relates to a protein that is highly homologous to known interleukin-1 cytokines, nucleic acid molecules that encode such a protein, antibodies that recognize the protein, and methods for diagnosing conditions related to host inflammatory and immune responses.

17 Claims, 15 Drawing Sheets

Figure 1

(A) SEQ ID 2: cDNA sequence  Underlined are start ATG codon and stop TAG codon

Gatcaggggttccaggaactcaggatctgcagtgaggaccagacaccactgattgcaggaatgtgttccc
tccccatgcaagatactacataattaaatatgcagaccaaggctctatacacaagagatggccagct
gctgtgggagatcctgttgcagacaactgctgtgcagagaagatctgcatacttcctaacagaggcttg
gcccgaccaaggtccccatttcctggggatccagggaggagcccgtgcctgcatgtgtggagacag
aagagggggccttcctacagagctgaggatgtgaacattgaaggaactgacaaaggtggtgaagaggccac
acgcttcaccttcttccagagcagcagctcaggctccgccttcagggcttgaggctgctgcctggctgg
ttcctgtgtggcccggcagagcccagcccagtgagccagcagctcaccaaggagagtgagccctcagccgta
ccaagtttacttgaacagagctggtagggagacaggaaactgc (B) SEQ ID 1: Amino Acid Sequence MCSLPMARYYIIKYADQKALYTRDGQLLVGDPVADNCCAEKICILPNRGLAR
TKVPIFLGIQGGSRCLACVETEEGPSLQLEDVNIEELYKGGEEATRFTFFQSSS
GSAFRLEAAAWPGWFLCGPAEPQQPVQLTKESEPSARTKFYFEQSW*

Human IL-1RP Exon/Intron Structure

Sequence ID NO: 4

Figure 2

```
   1 ATGCCCAGGC TCTTCTTCCT TCATGTCCTG CAGCCAATTA TAGAGATTGG
     TACGGGTCCG AGAAGAAGGA AGTACAGGAC GTCGGTTAAT ATCTCTAACC
  51 TGCAGGCCTG ACCCACCTGT ACCAGACGGT ATAAACACAG CGCAATGCCC
     ACGTCCGGAC TGGGTGGACA TGGTCTGCCA TATTTGTGTC GCGTTACGGG
 101 TGGAGAAATC AGTTGGAGTC TCCAGGGATC AGGGTTCCAG GAACTCAGGA
     ACCTCTTTAG TCAACCTCAG AGGTCCCTAG TCCCAAGGTC CTTGAGTCCT
 151 TCTGCAGGTC AGTGATGGAC AGGCAATATT CTCTCTCTCT TTTCTTTCTT
     AGACGTCCAG TCACTACCTG TCCGTTATAA GAGAGAGAGA AAAGAAAGAA
 201 TTCTACTCTC TGCTGTCAAT ATCTCTGGTA TGCCCTCTAT CCCTTCACTC
     AAGATGAGAG AGGACAGTTA TAGAGACCAT ACGGGAGATA GGGAAGTGAG
 251 CTCCTGGCAA GCTGTCTAGG TAACAAGGTA GTCCCCTCAT ATGACATGAT
     GAGGACCGTT CGACAGATCC ATTGTTCCAT CAGGGGAGTA TACTGTACTA
 301 GGGACATCAA AAACATTTAG GAGCACATAA AGAGATTTGA GGAGAAGGAA
     CCCTGTAGTT TTTGTAAATC CTGGTGTATT TCTCTAAACT CCTCTTCCTT
 351 TAGGTTAAGC CAAATCAAGA TTTCTGAACT ACTTAGAACA ACTGACTTTA
     ATCCAATTCG GTTTAGTTCT AAAGACTTGA TGAATCTTGT TGACTGAAAT
 401 GAAAGTAATC TCAAAAGAAA CCATCTGGGC CAATGGTATT CAAACCGTGT
     CTTTCATTAG AGTTTTCTTT GGTAGACCCG GTTACCATAA GTTTGGCACA
                 HindIII
 451 TTGGTGGAAG CTTAAGAGAT TTTTTGTTTT CGTTTTTTTT TTTTTGTGCT
     AACCACCTTC GAATTCTCTA AAAAACAAAA GCAAAAAAAA AAAAACACGA
 501 CCTTGGTAGC TCCTCAGTGT CTTCTTTGCA GGCAAGAGAA ATACTAGCAG
     GGAACCATCG AGGAGTCACA GAAGAAACGT CCGTTCTCTT TATGATCGTC
 551 GGTTCAAAG TCTCCATTGC TTCCTGTGTC AGCAAAGCAG CTGCCCTTTA
     CCAAGGTTTC AGAGGTAACG AAGGACACAG TCGTTTCGTC GACGGGAAAT
                         EcoRI
 601 TCCTTTTTAC AATCATTAGA ATTCTGCATA AAATTTTATT GTGAAACTTA
     AGGAAAAATG TTAGTAATCT TAAGACGTAT TTTAAAATAA CACTTTGAAT
 651 AAACAGTTTT GAAAGATACC TTACTCAATC TTTCCATCCA ATGTTGATAA
     TTTGTCAAAA CTTTCTATGG AATGAGTTAG AAAGGTAGGT TACAACTATT
 701 GTTGAAGGCC CAGGGATAAA AGGTGGCAAA ATAAATTGGT AGCAGAGCTA
     CAACTTCCGG GTCCCTATTT TCCACCGTTT TATTTAACCA TCGTCTCGAT
 751 GGTCTAGGAC TCAGCCTTTC TATTCAAAGT CTGCTCTGTG TGTTTCTATG
     CCAGATCCTG AGTCGGAAAG ATAAGTTTCA GACGAGACAC ACAAAGATAC
 801 TCCTGGCCAC AAGGACCAGG GTAGTTCAAT TAGGGTGGTT GGAGAGAGGT
     AGGACCGGTG TTCCTGGTCC CATCAAGTTA ATCCCACCAA CCTCTCTCGA
 851 TCAAGTGAGC TGTAAGCCAT GCTTCATGAC TTCAAGATCT TATAAACTTT
     AGTTCACTCG ACATTCGGTA CGAAGTACTG AAGTTCTAGA ATATTTGAAA
 901 TATAAGGGAA ACAAATATCT TTATGTACAA CAATAAATAA TACAGTAAAA
     ATATTCCCTT TGTTTATAGA AATACATGTT GTTATTTATT ATGTCATTTT
 951 TTTAATAGGA GTTCAGAGTA GAGTTACAAT AGTAAGGGAA AGATTCATTA
     AAATTATCCT CAAGTCTCAT CTCAATGTTA TCATTCCCTT TCTAAGTAAT
1001 AACTCTGAGT CATGGAATTA TAAATAGTTT GGCCTAGAAA GAACCTTCAT
     TTGAGACTCA GTACCTTAAT ATTTATCAAA CCGGATCTTT CTTGGAAGTA
1051 AACCACATAA TCTAATCCCA TGAATGTATA GTGCTGAAAC TGAGGGTTGG
     TTGGTGTATT AGATTAGGGT ACTTACATAT CACGACTTTG ACTCCCAACC
```

Figure 2
Continued

```
1101  AGGTAAAAG ACATAACCCT GTATGTCTAA GCTGTAACTC TACACTGGTA
      TCCAATTTTC TGTATTGGGA CATACAGATT CGACATTGAG ATGTGACCAT
1151  ATTAATTTGA TAGAACTAGA TACTGAACCC ATCTATACTG ATACTATCTC
      TAATTAAACT ATCTTGATCT ATGACTTGGG TAGATATGAC TATGATAGAG
1201  CAGTGATCTT AATATCAAAA GATCTGAATG GATGACAATG AGAAGGGATG
      GTCACTAGAA TTATAGTTTT CTAGACTTAC CTACTGTTAC TCTTCCCTAC
1251  ACTTTTGAGG CAGGGAGAAC AATGGGACAC CTGTGAGTAC GTCCACTGAG
      TGAAAACTCC GTCCCTCTTG TTACCCTGTG GACACTCATG CAGGTGACTC
1301  AAGATAAGAA AGGAATTATG TCGCCAGGAG GTGTGGTTA GTGTCCATCG
      TCTATTCTT TCCTTAATAC AGCGGTCCTC CACACCAAAT CACAGGTACC
1351  AGAAGTGAGA TGCTATCACA CAAGAAAATC AGTGCCAGAC GGTGACAAAA
      TCTTCACTCT ACGATAGTGT GTTCTTTTAG TCACGGTCTG CCACTGTTTT
1401  CAGTCAGTCA CTGTAGATTC TAGAGCTGGG CAGGGATGTG GTGAAAAAAA
      GTCAGTCAGT GACATCTAAG ATCTCAGCCC GTCCCTACAC CACTTTTTTT
1451  TCTTAGAAC GTGGGTCCAC ATTCCTCACA TAGGTTGGAA TGAATGAAAG
      AGAAATCTTG CACCCAGGTG TAAGGAGTGT ATCCAACCTT ACTTACTTTC
1501  GCAGAAAAAC CGGGAATACA AGTACAGTAG TAATGGCAAT TAAAACACA
      CGTCTTTTTG GCCCTTATGT TCATGTCATC ATTACCGTTA ATTTTTGTGT
1551  AAGTTATATT TTAAAGAAAT AACCTGTAGG GACTTGATAA GTTAGACACT
      TTCAATATAA AATTTCTTTA TTGGACATCC CTGAACTATT CAATCTGTGA
1601  GAGTCAGGAG AAGTAGGAGA TATTGTCAAT GAGTCTCAGG TTTTGAATAT
      CTCAGTCCTC TTCATCCTCT ATAACAGTTA CTCAGAGTCC AAAACTTATA
1651  CACTGGTCAG AGGAATATTA TGACAGTGAG AGAAATGAAA TTGGGAGGAA
      GTGACCACTC TCCTTATAAT ACTGTCACTC TCTTTACTTT AACCCTCCTT
1701  TGTGTGGGCT GGGAGGAGAA GATAATTAAC TTAACCTTAA ATATAATTGG
      ACACACCCGA CCCTCCTCTT CTATTAATTG AATTGGAATT TATATAAACC
1751  TTGGATATCA GCAGGATGTC CAAAGTGGGC TGTCCTGTAG GCTGCAGGAG
      AACCTATAGT CGTCCTACAG GTTTCACCCG ACAGGACATC CGACGTCCTC
1801  GTAAAGTGGG ATGTGCAGTC TACATTTGGG AGCCATTAGC CCAAGATAAT
      CATTTCACCC TACACGTCAG ATGTAAACCC TCGGTAATCG GGTTCTATTA
1851  CATTTCAGCT GTAGAAGTCA ATGAATTCA GCTTAATATG ATGTGAAATA
      GTAACGTCGA CATCTTCAGT TACTTAACGT CGAATTATAC TACACTTTAT
1901  GAAGTGCTTA GGACCTTCTT AGCCTTAGGG GTGGCCCCAG AAGGAGGTGA
      CTTCACGAAT CCTGGAACAA TCGGAATCCC CACCGGGGTC TTCCTCCACT
1951  AATCTACAAT GGGAGAAAGA GGTGTGAAGG GAGTCATTCA ATGTCAAGGG
      TTAGATGTTA CCCTCTTTCT CCACACTTCC CTCAGTAAGT TACAGTTCCC
2001  TTCCAAGGAG GCAATGACTA AATATCAAAG GAATCAAAAG AATCTCTGGA
      AAGGTTCCTC CGTTACTGAT TTATAGTTTC CTTAGTTTTC TTAGAGACCT
2051  TCTTTCTCCA CAGAAGTTAA TATTGGTCTT GGACAGAACA TCCCACATAG
      AGAACGAGGT GTCTTCAATT ATAACCAGAA CCTGTCTTGT AGGGTGTATC
2101  ATACTGTGCA GGAGAAATGAT GAAGGATAGG ACAGGGTGCT GTGCAAAGGA
      TATGACACGT CCTCTTACTA CTTCCTATCC TGTCCCACGA CACGTTTTCT
2151  ACATGGGGAA AGCCCAAGTT TAGCTGATGG CAGTGTTTGA GCCAGGACAG
      TGTACCCCTT TCGGGTTCAA ATCGACTACC GTCACAAACT CGGTCCTGTC
2201  GTGAATTGCG GAGGTCTGAG AGCCAGATGC CATGTCCAGT GAGAAATGAG
      CACTTAACGC CTCCAGACTC TCGGTCTACG GTACAGGTCA CTCTTTACTC
```

Figure 2
Continued

```
2251  AGGAAGAAAA GAGGGATATA GACTGAAGTT CAGTGAAAAG TCATTTGAGG
      TCCTTCTTTT CTCCCTATAT CTGACTTCAA GTCACTTTTC AGTAAACTCC
                                 HindIII
                                 ~~~~~~~
2301  AAAATAGGGA GGGGAAGCTT TGGGGGTGAG GCATGTGGCA CACTGGGAGG
      TTTTATCCCT CCCCTTCGAA ACCCCCACTC CGTACACCGT GTGACCCTCC
2351  GGCTTGGCAC ACAGCAGAGG TTCAGCACCA AGACCCAGGC TCTCTGATGG
      CCGAACCGTG TGTCGTCTCC AAGTCGTGGT TCTGGGTCCG AGAGACTACC
2401  ACCAGACGCT AGCTTCCTAC CCTTACTCAC TTCATCACAA TCTATCAGAA
      TGGTCTGCGA TCGAAGGATG GGAATGAGTG AAGTAGTGTT AGATAGTCTT
2451  CCCAGGCGGA GGGAGCCGAA TAGGGAGCC TTTGGGAAAG ACACTGTACA
      GGGTCCGCCT CCCTCGGCTT ATCCCCTCGG AAACCCTTTC TGTGACATGT
                                                BamHI
                                                ~~~~~~
2501  TTTTGGCTGT GCCAGAATGG GAGGTTTCTA GGGCCCATGG GATCCAGCTG
      AAAACCGACA CGGTCTTACC CTCCAAAGAT CCCGGGTACC CTAGGTCGAC
2551  GACTGGACCA GCATTGAATT TCTTCCAGCT CTTTGAGCTG ACACTGACCC
      CTGACCTGGT CGTAACTTAA AGAAGGTCGA GAAACTCGAC TGTGACTGGG
2601  AGAGTGGGAG TCATCAGCTT GCTATCCACC TTCACCCAGG GCCCTCCACT
      TCTCACCCTC AGTAGTCGAA CGATAGGTGG AAGTGGGTCC CGGGAGGTGA
2651  TTGTTGCCCC ATCTAGATCT GGGCACAGCT ACCACACTGC CCACTGTCCT
      AACAACGGGG TAGATCTAGA CCCGTGTCGA TGGTGTGACG GGTGACAGGA
2701  GCTGCTACAA CCAAAGAAGC CCCAGTGGTT TGGCCAAGGG GAGCCCATCA
      CGACGATGTT GGTTTCTTCG GGGTCACCAA ACCGGTTCCC CTCGGGTAGT
2751  TCAAGTGGGC TTGCATTGAG GCCATGATGC TGTTGAGTTA TCTGTACTGG
      AGTTCACCCG AACGTAACTC CGGTACTACG ACAACTCAAT AGACATGACC
2801  GGGATTGTCT AGTCCTTTAG GACTCAAAGT GCTGGCCAGG AGGAACCAGC
      CCCTAACAGA TCAGGAAATC CTGAGTTTCA CGACCGGTCC TCCTTGGTCG
2851  AGCATTGACA TCACCTGGTT GCATATTTGA AATGTACAGT CTCAGGCCCC
      TCGTAACTGT AGTGGACCAA CGTATAAACT TTACATGTCA GAGTCCGGGG
2901  ACCCCAGGCC TGAAAAACCA GAATCTGTTA TTTTAACAAG AACTGCAGGT
      TGGGGTCCGG ACTTTTTGGT CTTAGACAAT AAAATTGTTC TTGACGTCCA
2951  GGTTTATATA TTTATTAATA AGTGTGAAGA ATGGAATGAA AGTACACCAG
      CCAAATATAT AAATAATTAT TCACACTTCT TACCTTACTT TCATGTGGTC
3001  TTCCCAAGCA GCCTGGCTGA TTGCTGGAAT CACTCCAAGT CCTACTGAAT
      AAGGGTTCGT CGGACCGACT AACGACCTTA GTGAGGTTCA GGATGACTTA
3051  TAGAACCTTC GGCCCAGGAA ATAGTAATTA TACAGAGTCC CCCAGGTGAT
      ATCTTGGAAG CCGGGTCCTT TATCATTAAT ATGTCTCAGG GGGTCCACTA
3101  GCAGATGGGC AGGCACATTT AGGAGCCAAT GACTTTAACT AAACACTTCA
      CGTCTACCCG TCCGTGTAAA TCCTCGGTTA CTGAAATTGA TTTGTGAAGT
3151  TTTAAAAAAT GTTGAAACTT ACTTGATACT ACAAAGGAAA TTCATGTTCA
      AAATTTTTTA CAACTTTGAA TGAACTATGA TGTTTCCTTT AAGTACAAGT
3201  TTATAGGAAA ATGTTGATAT GTTTAAAAAA TTACTCATAA AGCCATAGGT
      AATATCCTTT TACAACTATA CAAATTTTTT AATGAGTATT TCGGTATCCA
3251  AAGTGGTGCA ACAACACGAG TAACATTTCT ATGTATGTGT CTCTATGTGT
      TTCACCACGT TGTTGTGCTC ATTGTAAAGA TACATACACA GAGATACACA
3301  GGATTTAAAT AGAATTACAG TGTACACTTG ATTTATAATC TGCATTTTTC
      CCTAAATTTA TCTTAATGTC ACATGTGAAC TAAATATTAG ACGTAAAAAG
```

Figure 2
Continued

```
                                              HindIII
                                              ~~~~~~~
      3351  ACCTAATATA TTTTGAAAAT TTTTATGTCC TAAAACAAGC TTCTATAATA
            TGGATTATAT AAAACTTTTA AAAATACAGG ATTTTGTTCG AAGATATTAT
      3401  TCATCTTTAA CAAACACATA CATCCTTATT TATTGAATTT TGCTATAATT
            AGTAGAAATT GTTTGTGTAT GTAGGAATAA ATAACTTAAA ACGATATTAA
      3451  TCTTAGCCAA TTACCTATTA CTGAAAATTC AGATTTTTTT CAACTTCTTG
            AGAATCGGTT AATGGATAAT GACTTTTAAG TCTAAAAAAA GTTGAAGAAC
      3501  CTATTGTAAA AAATTATGCA GTGAACATTT TTGTAAGTAA ACATTTGGGC
            GATAACATTT TTTAATACGT CACTTGTAAA AACATTCATT TGTAAACCCG
      3551  AATCCGTTAT TTTTCCTAAG AGTAAGGGAA ACACATGCAA TCACAAAGTA
            TTAGGCAATA AAAAGGATTC TCATTCCCTT TGTGTACGTT AGTGTTTCAT
      3601  TACAGAATGC TTTAAGACTT TCATTCACAG CACCAACATC CCTCCAGAAT
            ATGTCTTACG AAATTCTGAA AGTAAGTGTC GTGGTTGTAG GGAGGTCTTA
      3651  TTGCACTTGT TAGTCCCTAT TATCCTTCAC TCTAAGTCTC AAAGTCATAC
            AACGTGAACA ATCAGGGATA ATAGGAAGTG AGATTCAGAG TTTCAGTATG
      3701  CCCAAGGCCT GGGGACAGAA AATGACTTGT CCAAAGTGAC AGTGACAGAC
            GGGTTCCGGA CCCCTGTCTT TTACTGAACA GGTTTCACTG TCACTGTCTG
      3751  CCAGTACTAA AAGCCACCTT GGCTACAGCC CTGTTTCTGG AACTTGAGAG
            GGTCATGATT TTCGGTGGAA CCGATGTCGG GACAAAGACC TTGAACTCTC
      3801  CTGAGGTGGT TGGAAGCCGT ATCCTCAGCA CCCACCTGTT CCTTCTCACC
            GACTCCACCA ACCTTCGGCA TAGGAGTCGT GGGTGGACAA GGAAGAGTGG
      3851  TGCCTCCCCA GGGTCCCTCA GCATCTCTCT ATTCCTCCCT GAGCCCTATT
            ACGGAGGGGT CCCAGGGAGT CGTAGAGAGA TAAGGAGGGA CTCGGGATAA
      3901  ACTTTCTTCC ACCTGCCTTC TTCCTTTCTC TTCTCTCATT TTCTGCTTTC
            TGAAAGAAGG TGGACGGAAG AAGGAAAGAG AAGAGAGTAA AAGACGAAAG
      3951  TTATATTTTT TCTTCTCTAT TCCCTTCTTA TTTGGTGAGA ATCAGATCTA
            AATATAAAAA AGAAGAGATA AGGGAAGAAT AAACCACTCT TAGTCTAGAT
      4001  CTCGGTAAAC CTCAGCCCTA GTCATACTTG CGTTACTTTC CTGAGCTAAT
            GAGCCATTTG GAGTCGGGAT CAGTATGAAC GCAATGAAAG GACTCGATTA
      4051  TTCCAACTCC TGATTAGCTC TGGGTTTATT TCCATGCTAA ATTCTGGACT
            AAGGTTGAGG ACTAATCGAG ACCCAAATAA AGGTACGATT TAAGACCTGA
      4101  GGCCTTTCCA ATGGGTGTTC ATTTTAGGGA AGAGCTCTAG GACAGGATAA
            CCGGAAAGGT TACCCACAAG TAAAATCCCT TCTCGAGATC CTGTCCTATT
      4151  CCCATCGGGA AGGAGCAGAG TCATGTGAGG CTGTGTGGCC TGGCATTTAT
            GGGTAGCCCT TCCTCGTCTC AGTACACTCC GACACACCGG ACCGTAAATA
      4201  ACAGGGCCAC TATCTTCACT GTGCCATTTT CCATCTGGAA CAGAATGGGG
            TGTCCCGGTG ATAGAAGTGA CACGGTAAAA GGTAGACCTT GTCTTACCCC
      4251  GAGTTTGGAT GGGCTGTTTT CAGCAGTCTT GGCCAAGCAC TTCTAGTCAC
            CTCAAACCTA CCCGACAAAA GTCGTCAGAA CCGGTTCGTG AAGATCAGTG
      4301  TAGGAATGAT GTTTTCCAAC TCTCTGGGGA GACCCCACCA GCCTCACTGC
            ATCCTTACTA CAAAAGGTTG AGAGACCCCT CTGGGGTGGT CGGAGTGACG
      4351  TGCTGGAGAC CCCTTCTAGT TGTGCTCTCT TCTTTCACTC TGGGCTCTAG
            ACGACCTCTG GGGAAGATCA ACACGAGAGA AGAAAGTGAG ACCCGAGATC
      4401  TTATCTAACC CTTGGCTAGT TATGGGGGCG GTGGTGTGGT GCCCTGTTGG
            AATAGATTGG GAACCGATCA ATACCCCCGC CACCACACCA CGGGACAACC
```

Figure 2
Continued

```
4451 CCAACAGGGC AGTGGGACTG GGTTTGAGCT GGGCTTATCC TCCAACTGTG
     GGTTGTCCCG TCACCCTGAC CCAAACTCGA CCCGAATAGG AGGTTGACAC
4501 AGGGAGGCTA CAGCACACTC CACCCCACTC TCAGGGCTGG GAATTGTTGT
     TCCCTCCGAT GTCGTGTGAG GTGGGGTGAG AGTCCCGACC CTTAACAACA
4551 GGCTCAGCTA TTTGGGGGAA TCTGTTTTCC AGTTTCTCAG AACCAGCGCA
     CCGAGTCGAT AAACCCCCTT AGACAAAAGG TCAAAGAGTC TTGGTCGCGT
4601 AGCACACACA TCCCAGGCTC ACACCCCTGG TGGCTGGACT TGCTCCCGGA
     TCGTGTGTGT AGGGTCCGAG TGTGGGGACC ACCGACCTGA ACGAGGGCCT
4651 TAGCCTCAGT CAGGGAGAGG CAGAGCTGCC TGGAGCCTGC TGGGCTGGTG
     ATCGGAGTCA GTCCCTCTCC GTCTCGACGG ACCTCGGACG ACCCGACCAC
4701 GAAGCCTTGG TGGATTCTGG CAGGCCAATT ATAGACGAAT GGCCTGGGGA
     CTTCGGAACC ACCTAAGACC GTCCGGTTAA TATCTGCTTA CCGGACCCCT
4751 ACCCGTGCAG CCCTTGGCTG AGTGGTTCTA AGCCCCAGCA CGTCTGCCTC
     TGGGCACGTC GGGAACCGAC TCACCAAGAT TCGGGGTCGT GCAGACGGAG
4801 TGGCTTCACC CAGCCTCCTT TTCTAACTGC CCTTCTCTCC TCCCCATCAG
     ACCGAAGTGG GTCGGAGGAA AAGATTGACG GAAGAGAGG AGGGGTAGTC
                                       Met Cys Ser Leu Pro Met Ala Arg
4851 TGAGGACCAG ACACCACTGA TTGCAGGAAT GTGTTCCCTC CCCATGGCAA
     ACTCCTGGTC TGTGGTGACT AACGTCCTTA CACAAGGGAG GGGTACCGTT
     +1  Arg Tyr Tyr
4901 GATACTACAT GTAAGTTGTC CTGGCATGTC CCTGCTTTCC AAGCCAGGGG
     CTATGATGTA CATTCAACAG GACCGTACAG GGACGAAAGG TTCGGTCCCC
4951 GTCAGGGTGG GAAGAGGAAA GGAATGCTGA GTCAGAGGAT GAGGCTCCTT
     CAGTCCCACC CTTCTCCTTT CCTTACGACT CAGTCTCCTA CTCCGAGGAA
                                              HindIII
5001 CTCACCTTAG AAATTGCAAG TGCCCCATAA TTAAGCTTCA TCATCACCAC
     GAGTGGAATC TTTAACGTTC ACGGGGTATT AATTCGAAGT AGTAGTGGTG
5051 AGTAGCAACA GCTCTTTCCT GAACGTCTGC AAGATGCCAG CCAATCTACT
     TCATCGTTGT CGAGAAAGGA CTTGCAGACG TTCTACGGTC GGTTAGATGA
5101 GCCTCATCTC TGTTCCAAAA AGTCTGTAAG TGGAGTGTTA TTAAACCCAT
     CGGAGTAGAG ACAAGGTTTT TCAGACATTC ACCTCACAAT AATTTGGGTA
5151 TTTACAGATC TGGAAGCTGA GGCTCAAAGA GGGTAAATAA CTTCCCCCAT
     AAATGTCTAG ACCTTCGACT CCGAGTTTCT CCCATTTATT GAAGGGGGTA
5201 GTCACACAGC TACCAAAAGG CAGAGCCAGG AATCAGACTT CATGTCCTCT
     CAGTGTGTCG ATGGTTTTCC GTCTCGGTCC TTAGTCTGAA GTACAGGAGA
5251 GTGCTGCTCC ATCCGCCTCT CTGAAATGTC AGAAAGTTTT GAATCTCAAT
     CACGACGAGG TAGGCGGAGA GACTTTACAG TCTTTCAAAA CTTAGAGTTA
5301 GACAGCATCT TGATGGTGGT CCCTGTGGCC TTTACTCCCA GTGTGGGCTT
     CTGTCGTAGA ACTACCACCA GGGACACCGG AAATGAGGGT CACACCCGAA
5351 CTAACACTTA CTTACATTTC ATCTCATTTG AGATTTGCAT CCTTCCTTAT
     GATTGTGAAT GAATGTAAAG TAGAGTAAAC TCTAAACGTA GGAAGGAATA
5401 CTTTTACTAC TTTGTTGTCT GTGATTTTGT CATAAGCTCC TTTCAGGAAG
     GAAAATGATG AAACAACAGA CACTAAAACA GTATTCGAGG AAAGTCCTTC
5451 GAGGTGAGGC ATAAGAAAAA TCAAAGAGGA CTCTGGGACG CATTTCCTCT
     CTCCACTCCG TATTCTTTTT AGTTTCTCCT GAGACCCTGC GTAAAGGAGA
```

Figure 2
Continued

```
5501  GCTCCTCCCA TGGACCCTGT AATGTCCAGG GCTGTGTCCT GGACAAGGTG
      CGAGGAGGGT ACCTGGGACA TTACAGGTCC CGACACAGGA CCTGTTCCAC
5551  GGTGGGGAGC AGTCCTGGTC TCAAGGAGGT GACAGCCTGG CTGGGAAGCA
      CCACCCCTCG TCAGGACCAG AGTTCCTCCA CTGTCGGACC GACCCTTCGT
5601  AGACACATAC ATAGGAAGCA CATAAATGAC AAAGCAGATG TCAGCACTTC
      TCTGTGTATG TATCCTTCGT GTATTTACTG TTTCGTCTAC AGTCGTGAAG
5651  AGGGCATCTA ATCTGGGTTC TGGTCTCCAA ATAGAATGCT GCTGGCATGT
      TCCCGTAGAT TAGACCCAAG ACCAGAGGTT TATCTTACGA CGACCGTACA
5701  GAGTTGTCAC ATCTGGGTTG TCAAGGTGGC AAGGGGAATG CCAGTCAGCA
      CTCAACAGTG TAGACCCAAC AGTTCCACCG TTCCCCTTAC GGTCAGTCGT
5751  AGCCCAGGAT CTTTCCGGAA GTTTATTTTT ATTGTACAAG TGAACCTGCT
      TCGGGTCCTA GAAAGGCCTT CAAATAAAAA TAACATGTTC ACTTGGACGA
5801  TTAAATATGT ACAGTCATTA GCTAAGGGTA TTATCGTTAG CTGTTATTGA
      AATTTATACA TGTCAGTAAT CGATTCCCAT AATAGCAATC GACAATAACT
5851  GATAGAAAAA TCCCCTGGAG GTGGTGGAAT TTGTCCAGAG GTTCTGCCCT
      CTATCTTTTT AGGGGACCTC CACCACCTTA AACAGGTCTC CAAGACGGGA
5901  AAAAGGTTAA TGAGAGCTCT CCAGCCCTGA CAGCAGCTGA CAGGCATCTT
      TTTTCCAATT ACTCTCGAGA GGTCGGGACT GTCGTCGACT GTCCGTAGAA
5951  TGAAACCAAC TAGGTGACTG AGCTAATACC CTGCATGACT TTGAAGCCTT
      ACTTTGGTTG ATCCACTGAC TCGATTATGG GACGTACTGA AACTTCGGAA
6001  TAAAATATCT GAAAAGCAAA TCACACTTCA GTATACACTC AATCTCTGTA
      ATTTTATAGA CTTTTCGTTT AGTGTGAAGT CATATGTGAG TTAGAGACAT
6051  CTAAAGAGAA TAAACATTTA TAAACAATTA GGGCAGGCCC AAAAAATTTA
      GATTTCTCTT ATTTGTAAAT ATTTGTTAAT CCCGTCCGGG TTTTTTAAAT
6101  AGATAAGGTC CACTGTATCC CAAAGTCATC TGAGCCTCAC TAAGAAATTT
      TCTATTCCAG GTGACATAGG GTTTCAGTAG ACTCGGAGTG ATTCTTTAAA
6151  CTCAGGAAGC CAGGAACATT TTCTTTACCC CTCTGTCAGA GGGCATTGGC
      GAGTCCTTCG GTCCTTGTAA AAGAAATGGG GAGACAGTCT CCCGTAACCG
6201  TCTCCGTTCT CCTCTGAAGG CCTCCCCAAG CCATGAGAAG GCAGGAAGCA
      AGAGGCAAGA GGAGACTTCC GGAGGGGTTC GGTACTCTTC CGTCCTTCGT
6251  CAGCCTCTGA AAAGCAAGAA CACAGGAGAC CTTCCTTGCT TTAAGGCTGG
      GTCGGAGACT TTTCGTTCTT GTGTCCTCTG GAAGGAACGA AATTCCGACC
6301  CCTGGTCTTT ACCTGCTCTT GGGAGTGACC ATTCCCCTCT TACCACCTGT
      GGACCAGAAA TGGACGAGAA CCCTCACTGG TAAGGGGAGA ATGGTGGACA
6351  GAAGGAGAGA AAATCGCCCA AATGCTCAAG GTGGTGATTC AGAGCATGGA
      CTTCCTCTCT TTTAGCGGGT TTACGAGTTC CACCACTAAG TCTCGTACCT
6401  AGTGGAAGGG CTTGGGGGCC AGTGGTGCAT AAAGGGAATG GGCCATCAGC
      TCACCTTCCC GAACCCCCGG TCACCACGTA TTTCCCTTAC CCGGTAGTCG
+2                                 Ile Lys Tyr Ala Asp Gln Lys Ala Leu Tyr Thr
6451  ACTGTCATAC TGTTTCAGAA TTAAATATGC AGACCAGAAG GCTCTATACA
      TGACAGTATG ACAAAGTCTT AATTTATACG TCTGGTCTTC CGAGATATGT
+2    -Thr Arg Gly Gln Leu Leu Val Gly Asp Pro Val Ala Asp Asn Cys Cys
6501  CAAGAGATGG CCAGCTGCTG GTGGGAGATC CTGTTGCAGA CAACTGCTGT
      GTTCTCTACC GGTCGACGAC CACCCTCTAG GACAACGTCT GTTGACGACA
```

Figure 2
Continued

```
           +2   Ala
         6551   GCAGGTGAGC TTCTGGGGCC TCCACCCCAT GCTCCATCTG CCATAGGCCC
                CGTCCACTCG AAGACCCCGG AGGTGGGGTA CGAGGTAGAC GGTATCCGGG
         6601   TCCCTTCTCT TCTTCCCTTT CCTCCCCAGC AGAGGGTCAG CAGCTGCCCC
                AGGGAAGAGA AGAAGGGAAA GGAGGGGTCG TCTCCCAGTC GTCGACGGGG
         6651   CAGTGACAGT GAGAAGGGCC AGAGAGCAGC TGTGGCCTCT CCTAGCGAGG
                GTCACTGTCA CTCTTCCCGG TCTCTCGTCG ACACCGGAGA GGATCGCTCC
         6701   GGACATGACT CCTGCAGAAG TCCTGGCTCA CCGTCCAGTC TGCATGCAGG
                CCTGTACTGA GGACGTCTTC AGGACCGAGT GGCAGGTCAG ACGTACGTCC
         6751   GCCAGGCCAG GTGTGCCCAT GTCCAGTTCC TTCCTGCCTG AGCCTTTACC
                CGGTCCGGTC CACACGGGTA CAGGTCAAGG AAGGACGGAC TCGGAAATGG
         6801   TGCCAAGAGC CTGCAACATG GGGTTCCCTT GTCCCTTGAC TCTTCTCTCT
                ACGGTTCTCG GACGTTGTAC CCCAAGGGAA CAGGGAACTG AGAAGAGAGA
           +1                               Lys Ile Cys Ile Leu Pro Asn Arg Gly Leu Ala Arg
         6851   CTTCCCTCCT AGAGAAGATC TGCATACTTC CTAACAGAGG CTTGGCCCGC
                GAAGGGAGGA TCTCTTCTAG ACGTATGAAG GATTGTCTCC GAACCGGGCG
                                                 BamHI
           +1   Thr Lys Val Pro Ile Phe Leu Gly Ile Gln Gly Gly Ser Arg Cys Leu Ala
         6901   ACCAAGGTCC CCATTTTCCT GGGGATCCAG GGAGGGAGCC GCTGCCTGGC
                TGGTTCCAGG GGTAAAAGGA CCCCTAGGTC CCTCCCTCGG CGACGGACCG
           +1   Ala Cys Val Glu Thr Glu Glu Gly Pro Ser Leu Gln Leu
         6951   ATGTGTGGAG ACAGAAGAGG GGCCTTCCCT ACAGCTGGAG GTGAGAGGCC
                TACACACCTC TGTCTTCTCC CCGGAAGGGA TGTCGACCTC CACTCTCCGG
         7001   TCTCCCCATT CTAGGGGACA CTGCAGACCT GGCCTGACCC CTGGGATGCT
                AGAGGGGTAA GATCCCCTGT GACGTCTGGA CCGGACTGGG GACCCTACGA
         7051   CTGGCATCTT TGTGCCTATC TGTGGATTCC CAGCCAGGTC CACATGTCCT
                GACCGTAGAA ACACGGATAG ACACCTAAGG GTCGGTCCAG GTGTACAGGA
         7101   ACTTCCTCAG GTTTCCACCA TCTCCCTCTG CACCTAGCAC CAAGACCCTT
                TGAAGGAGTC CAAAGGTGGT AGAGGGAGAC GTGGATCGTG GTTCTGGGAA
         7151   GCCCTCTAGA ATCTGCAGAA GGCAGTCCCT TGGGTAAAAA CCAGCCCTGT
                CGGGAGATCT TAGACGTCTT CCGTCAGGGA ACCCATTTTT GGTCGGGACA
         7201   CAGGTCCTTT TTTGGCCAAG CCCCAGAGGC CTCCAGGGCT AACACCTCCA
                GTCCAGGAAA AAACCGGTTC GGGGTCTCCG GAGGTCCCGA TTGTGGAGGT
           +2                                                     Asp Val Asn
         7251   TCAGCACTCT CATTCTGCAG CCATCCACCT TGCCCCCACA GGATGTGAAC
                AGTCGTGAGA GTAAGACGTC GGTAGGTGGA ACGGGGGTGT CCTACACTTG
           +2   Ile Glu Glu Leu Tyr Lys Gly Gly Glu Glu Ala Thr Arg Phe Thr Phe Phe
         7301   ATTGAGGAAC TGTACAAAGG TGGTGAAGAG GCCACACGCT TCACCTTCTT
                TAACTCCTTG ACATGTTTCC ACCACTTCTC CGGTGTGCGA AGTGGAAGAA
           +2   Phe Gln Ser Ser Ser Gly Ser Ala Phe Arg Leu Glu Ala Ala Ala Trp Pro Gly
         7351   CCAGAGCAGC TCAGGCTCCG CCTTCAGGCT TGAGGCTGCT GCCTGGCCTG
                GGTCTCGTCG AGTCCGAGGC GGAAGTCCGA ACTCCGACGA CGGACCGGAC
           +2   Gly Trp Phe Leu Cys Gly Pro Ala Glu Pro Gln Gln Pro Val Gln Leu Thr
         7401   GCTGGTTCCT GTGTGGCCCG GCAGAGCCCC AGCAGCCAGT ACAGCTCACC
                CGACCAAGGA CACACCGGGC CGTCTCGGGG TCGTCGGTCA TGTCGAGTGG
```

Figure 2
Continued

```
         +2    Lys Glu Ser Glu Pro Ser Ala Arg Thr Lys Phe Tyr Phe Glu Gln Ser Trp
       7451    AAGGAGAGTG AGCCCTCAGC CCGTACCAAG TTTTACTTTG AACAGAGCTG
               TTCCTCTCAC TCGGGAGTCG GGCATGGTTC AAAATGAAAC TTGTCTCGAC
         +2    Trp
       7501    GTAGGGAGAC AGGAAACTGC GTTTTAGCCT TGTGCCCCCA AACTAAGCTC
               CATCCCTCTG TCCTTTGACG CAAAATCGGA ACACGGGGGT TTGATTCGAG
       7551    ATCCTGCTCA GGGTCTATGG TAGGCAGAAT AATGTCCCCC GAAATATGTC
               TAGGACGAGT CCCAGATACC ATCCGTCTTA TTACAGGGGG CTTTATACAG
       7601    CACATCCTAA TCCCAAGATC TGTGCATATG TTACCATACA TGTCCAAAGA
               GTGTAGGATT AGGGTTCTAG ACACGTATAC AATGGTATGT ACAGGTTTCT
```

Figure 3

Comparison of the IL-1 family of proteins

```
IL-1RA     ------------------------------------------------------------ ----------------------------------RPSGRKESRMQAF
FILdelta   ------------------------------------------------------------ ------------------------------------MVLSGALCF
IL-1H1     ------------------------------MRGTPGDADGGGR----------------- ----------------------------------AVYQSMCKPIPG
ILepsilon  ------------------------------------------M----------------- ------------------------------------EKALKIDTPQQG
FILzeta    -----------------------------MSGCDRRETETKGKNSFKKR-----------  --------------------------------------GPKVKNLNPKKF
IL1H4      MSFVGENSGVRMGSEDWEKDERQCCLEDPAGSPLEPGPSLPTMNFVHTSFKVKGNLNPKKF
IL1rp      ------------------------------------------------------------ ----------------------------------MCSLPMARYX
IL-1beta   ------------------------------------------------------------ ------------------------------------APVR-SLNC
IL1H2      ------------------------------------------------------------ ------------------------------------MNPQREAAPKSY
IL-1A      ------------------------------------------------------------ ------------------------------------SAPFSFLSNVKY
IL-18      ------------------------------------------------------------ ------------------------------------IFGKLESKLS IL-1RA     RIWDVNQKTFYLRNNQLVAG----------YLQGPNVNLEEKIDVVP---------IEPHALFLGI
FILdelta   RMKDSRLKVLYLENNQLLAG----------GLHAGKVIKGEEISVVPNRWLD-ASLSPVILGV
IL-1H1     TINDLNQQVWTLQGQNLVAVPRS-------DSVTP-VTVAVTICKYPEALEQ-GRGDPIYLGI
ILepsilon  SIQDINHRNWVLQDQTIAVFRK--------DRMSP-VTLALISCREVETLEK-DRGNPIYLGL
FILzeta    SIHDQDHKVLVLDSGNLIAVPDK-------NYIRPEIFFALASSLSBASAE---KGSPILLGV
IL1H4      SIHDQDEKTLVLDSGNLIAVPDK-------NYIRPEIFFALASSLSBASAE---KGSPILLGV
IL1rp      LIKYADQKALYTRDGQLLVG----------DPVAD-NCCAEKICLLENRGLA-RTKVPIFLGI
IL-1beta   TLRDSQQKSLVMSGPYELKALHL-------QGDMEQQVVFSMSFVQGEES--NDKLPVALGL
IL1H2      ALRDSBQMWVLSGNSLIARPLS--------RSIKP-VTLHLIACRDTEFSDK-EKGNMVYLGI
IL-1A      NFMRIIKYEFILMDALNQSIIRANDQYLTAAAHNLDEAVKFDMGAYKSSKDDAKITVLL
IL-18      VIRNLNDQVLFIDQGHRBLFED--------MTDSDCRDNAPRTIFIISMYK--DSQDRGMAV IL-1RA     HGGKMCLSCVK-SGD-ETRLQEAVNITDLSENRKQDK-RFAFIRSDSGPTTSFESAACP
FILdelta   QGGSQCLSCG---VGG-EPTLTLEHVNIMELILGRAKESK-SFTLFYRRDMGLTSSFESAAYP
IL-1H1     QNPEMCLXCEK--VGB-QPTLQLKEQKIMDLYGQPEPVK-PFLFYRAKTGRGSTLESVAFP
ILepsilon  NGLNLCLMCAK--VGD-QPTLQLKEKDIMDLYNQPEPVK-SFLFYHSQSGRNSTFESVAFP
FILzeta    SKGEFCLYCDKDKGQSHPSIQLKKEKIMKLAAQKESARRPFIFYRAQVGSWNMLESARHP
IL1H4      SKGEFCLYCDKDKGQSHPSIQLKKEKIMKLAAQKESARRPFIFYRAQVGSWNMLESARHP
IL1rp      QGGSRCLACVE-TEB-GPSLQLEDVNIEELYKGGEEAT-RFTFFQSSSGSAFRLEARHWP
IL-1beta   KEKNLYLSCVLKDDK--PTLQLESVDPKNYPKKKMEKR--FVFNKIEIANNKLEFESAQFP
IL1H2      KGKDICLFCAEIQGK--PTLQLKLQGSQDNIGKDTCWLVGIHTC-INLDVRESCFMGTLD
IL-1A      RISKTQLRVTAQDED-QPVLLKEMPEIPKTITGSETNL--LFFWE-THGTKNFFTSVAHP
IL-18      TISVKCEKISTLSCE-NKIISFKEMNPPDNIKDTKSDLIFFQRSVFGHDNKMQFESSSXE IL-1RA     GWFLCTAMEADQPVSLTNMPDEG----VMVTKFYFQEDE---------------
FILdelta   GWFLCTVPEADQPVRLTQIPENGGWNAPITNDFYFQQCD---------------
IL-1H1     DWFIASGKRD-QPIILTSELGKS----YNTAFELNIND----------------
ILepsilon  GWFIAVSSEGGCPLLITQELGKA----NTTDFGLTMLF----------------
FILzeta    GWFICTSCMCNEPVGVTDKFENR----KHIEFSFQPVCKAEMSPSEVSD
IL1H4      GWFICTSCMCNEPVGVTDKFENR----KHIEFSFQPVCKARMS-----------
IL1rp      GWFLCGPAEPQQPVQLTKESEPS----ARTKFYFSQSW----------------
IL-1beta   NWYISTSQAENMPVFLGGTKGGQ----DITDFTMQFVSB---------------
IL1H2      QWGIGVGRRK--WKSSFQHHHLRK---KDRDFSSMRTNIGMPG-----------
IL-1A      NLFIATKQDY-----NVCLAGGPP---STDFQILENQA----------------
IL-18      GYFLACEKERDLFKLILKKEDELG---DRSIMFTVQNED---------------
```

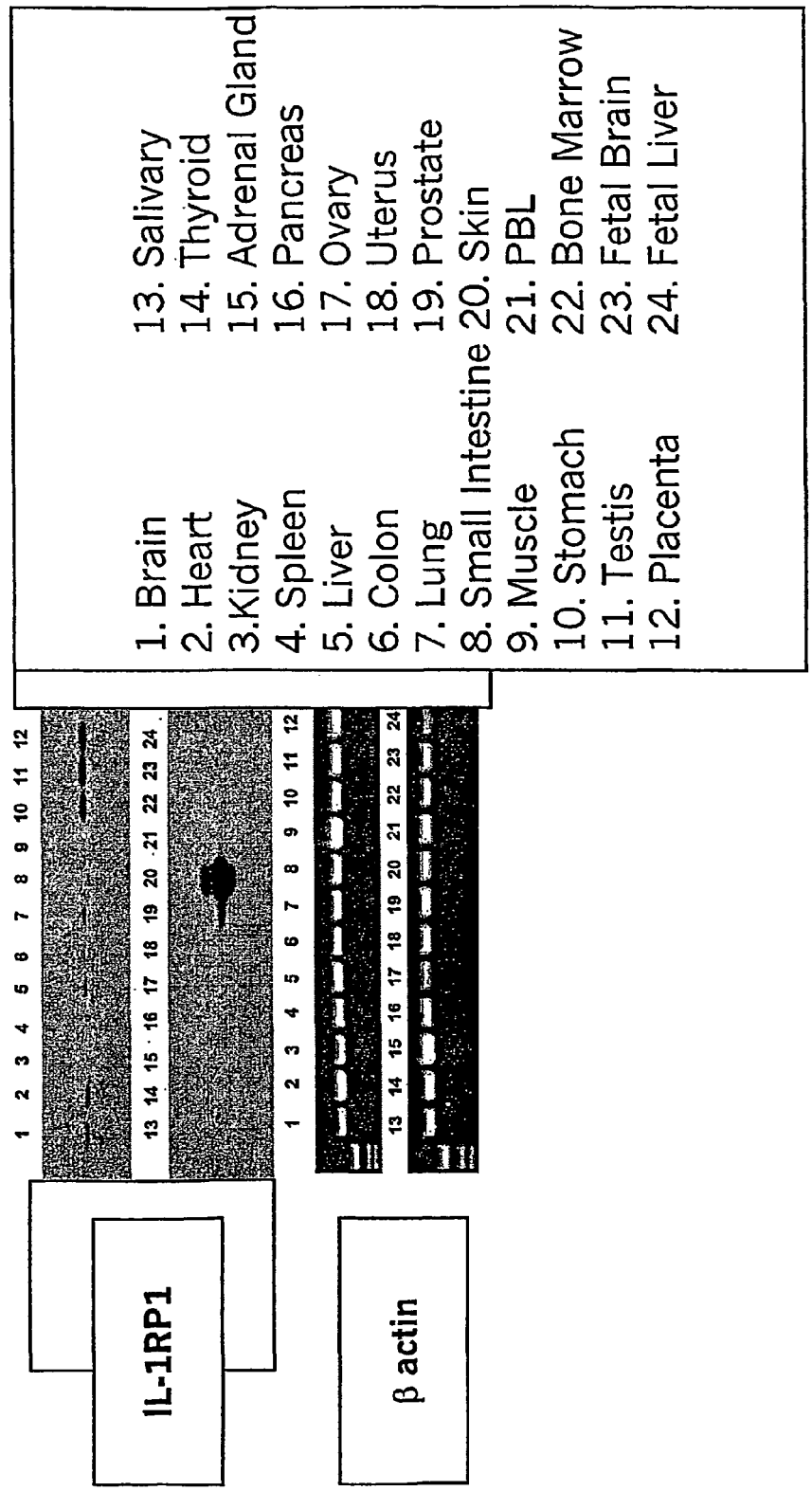
Figure 4. Expression of IL-1RP1 in different human tissues

IL-1RP1 primary sequence

Exon/Intron Structure of Human IL-1RP1

Il-1RP genomic sequence was identified within clone gnl|HUM_IDS..Contig|51735008 7800000561682013772180813148134110006819499950 of Celera Human Genome Database Partial sequence (16551-24200 bp) of human genomic Contig 51735008 (48134 bp) overlapping with hIL-1RP coding sequence is shown. Restriction sites of Bam HI (Bam), Eco RI (RI) and Hind III (HIII) are indicated.

Partial Sequence of human genomic Contig 51735008

Figure 8

```
  1  GATCAGGGTT CCAGGAACTC AGGATCTGCA GTGAGGACCA GACACCACTG ATTGCAGGAA TGTGTTCCCT CCCCATGGCA
     CTAGTCCCAA GGTCCTTGAG TCCTAGACGT CACTCCTGGT CTGTGGTGAC TAACGTCCTT ACACAAGGGA GGGGTACCGT

81  AGATACTACA TAATTAAATA TGCAGACCAG AAGGCTCTAT ACACAAGAGA TGGCCAGCTG CTGGTGGGAG ATCCTGTTGC
     TCTATGATGT ATTAATTTAT ACGTCTGGTC TTCCGAGATA TGTGTTCTCT ACCGGTCGAC GACCACCCTC TAGGACAACG

161  AGACAACTGC TGTGCAGAGA AGATCTGCAT ACTTCCTAAC AGAGGCTTGG CCCCGCACCAA GGTCCCCATT TTCCTGGGGA
     TCTGTTGACG ACACGTCTCT TCTAGACGTA TGAAGGATTG TCTCCGAACC GGGCGTGGTT CCAGGGGTAA AAGGACCCCT

241  TCCAGGGAGG GAGCCGCTGC CTGGCATGTG TGGAGACAGA AGAGGGGCCT TCCCTACAGC TGGAGGATGT GAACATTGAG
     AGGTCCCTCC CTCGGCGACG GACCGTACAC ACCTCTGTCT TCTCCCCGGA AGGGATGTCG ACCTCCTACA CTTGTAACTC

321  GAACTGTACA AAGGTGGTGA AGAGGCCACA CGCTTCACCT TCTTCCAGAG CAGCTCAGGC TCCGCCTTCA GGCTTGAGGC
     CTTGACATGT TTCCACCACT TCTCCGGTGT GCGAAGTGGA AGAAGGTCTC GTCGAGTCCG AGGCGGAAGT CCGAACTCCG

401  TGCTGCCTGG CCTGGTCTGG TCCTGTGTGG CCCGGGCAGAG CCCCAGCAGC CAGTACAGCT CACCAAGGAG AGTGAGCCCT
     ACGACGGACC GGACCAGACC AGGACACACC GGGCCCGTCTC GGGGTCGTCG GTCATGTCGA GTGGTTCCTC TCACTCGGGA

481  CAGCCCGTAC CAAGTTTTAC TTTGAACAGA GCTGGTAGGG AGACAGGAAA CTGC
     GTCGGGCATG GTTCAAAATG AAACTTGTCT CGACCATCCC TCTGTCCTTT GACG
```

Double Stranded Nucleotide sequence of IL-1RP1 cDNA

INTERLEUKIN-1 RELATED GENE AND PROTEIN

FIELD OF THE INVENTION

This invention relates to an interleukin-1 related gene and gene product. In particular, the invention relates to a protein that is highly homologous to known interleukin-1 cytokines, nucleic acid molecules that encode such a protein, antibodies that recognize the protein, and methods for diagnosing conditions related to host inflammatory and immune responses.

BACKGROUND OF THE INVENTION

The proinflammatory cytokine interleukin-1 (IL-1) elicits a wide array of biological activities that initiate and promote the host response to pathophysiological states including infection, fever, sleep, loss of appetite, acute phase protein synthesis, chemokine production, adhesion molecule upregulation, vasodilation, the coagulant state, increased hematopoiesis, and production and release of matrix metalloproteinases and growth factors. Until recently IL-1 activity was thought to reside in each of two molecules, IL-1 alpha (IL-1$\alpha$) and IL-1 beta (IL-1$\beta$), which are potent inflammatory cytokines that play important roles in host immune responses and in the development of inflammatory and autoimmune diseases. While only being about 25% identical, the two cytokines interact with and activate the same receptor complex, composed of the IL-1 Type-I receptor (IL-1RI) and IL-1 Receptor Accessory Protein (IL-1RAP) subunits. Upon binding and receptor activation, a number of signal transduction pathways are activated including that controlled by NF-kappa B. In fact, IL-1$\alpha$ and IL-1$\beta$ are thought to positively or negatively modulate NF-kB and AP-1 signaling stimulated through IL-1RI-associated kinase/TNF receptor-associated factor-like complexes recruited through the IL-1 receptor family. IL-1 induces expression of a large number of genes including cytokines, growth factors, cell adhesion molecules transcription factors and proteases. In addition to the agonist peptides, a third IL-1, IL-1 receptor antagonist protein (IL-1RA) can bind to IL-1 receptors and block activity of IL-1$\alpha$ and IL-1$\beta$. The IL-1 system has been shown to effect a number of inflammatory diseases in animals and in humans. Blockade of IL-1 signalling with an antibody to either of IL-1$\alpha$, IL-1$\beta$or the IL-1RI blocks the development of the disease processes in animal models of arthritis, encephalitis, contact sensitivity, graft rejection, endotoxic shock and inflammatory bowel disease among others. In addition, the recombinant IL-1 receptor antagonist protein has been shown to block the progression of rheumatoid arthritis in human clinical trials.

Recent studies have shown the IL-1 system is represented by a family of related genes. One IL-1 related gene is IL-18. This cytokine was originally cloned by its ability to induce gamma interferon expression. It was later shown that this molecule had significant structural homology to IL-1 and subsequently shown to bind to receptors highly related, but distinct from the IL-1RI and IL-1RAP. Another member of the family, the IL-1 receptor antagonist (IL-1RA), also binds to IL-1RI but fails to induce the subsequent interaction with IL-1RAP, thus not only not signaling itself, but also, by blocking the receptor, preventing the action of agonist IL-1s. Recently, 4 new IL-1 related molecules have been identified. These proteins share between 13 and 50% identify to the characterized IL-1 molecules. In this respect, two reports have identified overlapping but nonidentical sets of IL-1 related genes including IL-1H1, IL-1H2, IL-1H3 and IL-H4 (Kumar et al., J. Biol. Chem. 275 (2000), 10308–10314), and FIL$\delta$, FIL$\epsilon$, FIL$\nu$ and FIL$\zeta$ (Smith et al., J. Biol. Chem. 275 (2000),1169–1175). Several of these genes are either identical or clearly derived from the same gene including IL-1H2 and FIL$\nu$, IL-1H3 and FIL$\delta$, and IL-1H4 and FIL$\zeta$. IL-1H4 and FIL$\zeta$ are 88% identical with changes only at the extreme ends of cDNAs. Thus, these two sequences are derived from alternative splicing of the same gene. Interestingly, most of these molecules are relatively more related to IL-1 RA than to either IL-1$\alpha$, IL-1$\beta$ or IL-18, implying that common, IL-1 antagonizing, effect of these molecules may coincide with separate, unique activities. Importantly, while related at the amino acid level, none of the IL-1 related proteins appears to bind to the known IL-1 receptors.

SUMMARY OF THE INVENTION

The present invention relates to interleukin-1 cytokines, in particular to a novel interleukin-1 related polypeptide 1 (IL-1RP1).

In a first aspect, the invention provides an isolated polypeptide comprising an amino acid sequence as set forth in SEQ ID NO:1. Furthermore, the invention provides an isolated polypeptide consisting of an amino acid sequence as set forth in SEQ ID NO:1. The amino acid sequence as set forth in SEQ ID NO:1 shows a considerable degree of homology to that of known members of the family of interleulin-1 polypeptides. For convenience, the polypeptide consisting of the amino acid sequence as set forth in SEQ ID NO:1 will be designated as interleukin-1 related polypeptide 1, or IL-1RP1. Such a polypeptide, or a fragment thereof, is expressed in various tissues, predominantly in slin, like another known member of the interleukin-1 polypeptide family. Fragments of the isolated polypeptide having an amino acid sequence as set forth in SEQ ID NO:1 will comprise polypeptides comprising from about 5 to 152 amino acids, preferably from about 10 to about 152 amino acids, more preferably from about 20 to about 100 amino acids, and most preferably from about 20 to about 50 amino acids. Such fragments also form a part of the present invention. In accordance with this aspect of the invention there are provided novel polypeptides of human origin as well as biologically, diagnostically or therapeutically useful fragments, variants and derivatives thereof, variants and derivatives of the fragments, and analogs of the foregoing.

In a second aspect, the invention provides an isolated DNA comprising a nucleotide sequence that encodes a polypeptide as mentioned above. In particular, the invention provides (1) an isolated DNA comprising the nucleotide sequence as set forth in SEQ ID NO:2; (2) an isolated DNA comprising the nucleotide sequence set forth in SEQ ID NO:3; (3) an isolated DNA capable of hybridizing under high stringency conditions to the nucleotide sequence set forth in SEQ ID NO:3; and (4) an isolated DNA comprising the nucleotide sequence set forth in SEQ ID NO:4. Also provided are nucleic acid sequences comprising at least about 15 bases, preferably at least about 20 bases, more preferably a nucleic acid sequence comprising about 30 contiguous bases of SEQ ID NO:2 or SEQ ID NO:3. Also within the scope of the present invention are nucleic acids that are substantially similar to the nucleic acid with the nucleotide sequence as set forth in SEQ ID NO:2 or SEQ ID NO:3. In a preferred embodiment, the isolated DNA takes the form of a vector molecule comprising at least a fragment of a DNA of the present invention, in particular comprising the DNA consisting of a nucleotide sequence as set forth in SEQ ID NO:2 or SEQ ID NO:3.

A third aspect of the present invention encompasses a method for the diagnosis of conditions associated with host inflammatory or immune responses in a human which includes detecting elevated transcription of messenger RNA transcribed from the natural endogenous human gene encoding the novel polypeptide consisting of the amino acid sequence set forth in SEQ ID NO:1 in an appropriate tissue or cell from a human, where such elevated transcription is diagnostic of the human's affliction with such a condition. In particular, the said natural endogenous human gene encoding the novel polypeptide consisting of the amino acid sequence set forth in SEQ ID NO:1 comprises the genomic nucleotide sequence set forth in SEQ ID NO:4. In one embodiment of the present invention, the diagnostic method comprises contacting a sample of said appropriate tissue or cell or contacting an isolated RNA or DNA molecule derived from that tissue or cell with an isolated nucleotide sequence of at least about 15–20 nucleotides in length that hybridizes under high stringency conditions with the isolated nucleotide sequence encoding the novel polypeptide having an amino acid sequence set forth in SEQ ID NO:1. Another embodiment of the assay aspect of the invention provides a method for the diagnosis of certain diseases associated with host inflammatory or immune responses in a human which requires measuring the amount of the polypeptide of SEQ ID NO:1 or fragments thereof in a certain tissue or cell from a human suffering from such a disease, where the presence of an elevated amount of the polypeptide or fragments thereof, relative to the amount of the polypeptide or fragments thereof in the respective tissue or cell of a healthy individual is diagnostic of the human's suffering from conditions associated with host inflammatory or immune responses.

In accordance with one embodiment of this aspect of the invention there are provided anti-sense polynucleotides that can regulate transcription of the gene encoding the novel interleukin-1 related polypeptide 1; in another embodiment, double stranded RNA is provided that can regulate the transcription of the gene encoding the novel IL-1RP1.

Another aspect of the invention provides a process for producing the aforementioned polypeptides, polypeptide fragments, variants and derivatives, fragments of the variants and derivatives, and analogs of the foregoing. In a preferred embodiment of this aspect of the invention there are provided methods for producing the aforementioned interleukin-1 related peptide 1 comprising culturing host cells having incorporated therein an expression vector containing an exogenously-derived nucleotide sequence encoding such a polynucleotide under conditions sufficient for expression of the polypeptide in the host cell, thereby causing expression of the polypeptide, and optionally recovering the expressed polypeptide. In a preferred embodiment of this aspect of the present invention, there is provided a method for producing polypeptides comprising or consisting of an amino acid sequence as set forth in SEQ ID NO:1, which comprises culturing a host cell having incorporated therein an expression vector containing an exogenously-derived polynucleotide encoding a polypeptide comprising or consisting of an amino acid sequence as set forth in SEQ ID NO:1, under conditions sufficient for expression of such a polypeptide in the host cell, thereby causing the production of an expressed polypeptide, and optionally recovering the expressed polypeptide. Preferably, in any of such methods the exogenously derived polynucleotide comprises or consists of the nucleotide sequence set forth in SEQ ID NO:2, the nucleotide sequence set forth in SEQ ID NO:3, or the nucleotide sequence set forth in SEQ ID NO:4. In accordance with another aspect of the invention there are provided products, compositions, processes and methods that utilize the aforementioned polypeptides and polynucleotides for, inter alia, research, biological, clinical and therapeutic purposes.

In certain additional preferred embodiments of this aspect of the invention there is provided an antibody or a fragment thereof which specifically binds to a polypeptide that comprises the amino acid sequence set forth in SEQ ID NO:1, i.e., IL-1RP1. In certain particularly preferred embodiments in this regard, the antibodies are highly selective for human IL-1RP1-polypeptides or portions of human IL-1RP1 polypeptides.

In a further aspect, an antibody or fragment thereof is provided that binds to a fragment or portion of the amino acid sequence set forth in SEQ ID NO:1.

In another aspect, methods of treating a disease in a subject, where the disease is mediated by or associated with an increase or decrease in IL-1RP1 gene expression or an increase or decrease in the presence of IL-1RP1 polypeptide in a certain tissue or cell by the administration of an effective amount of an antibody that binds to a polypeptide with the amino acid sequence set out in SEQ ID NO:1, or a fragment or portion thereof to the subject are provided. Also provided are methods for the diagnosis of a disease or condition associated with an increase or decrease in IL-1RP1 gene expression or an increase or decrease in the presence of the IL-1RP1 polypeptide in a subject, which comprises utilizing an antibody that binds to a polypeptide with the amino acid sequence set out in SEQ ID NO:1, or a fragment or portion thereof, in an immunoassay.

In yet another aspect, the invention provides host cells which can be propagated in vitro, preferably vertebrate cells, in particular mammalian cells, or bacterial cells, which are capable upon growth in culture of producing a polypeptide that comprises the amino acid sequence set forth in SEQ ID NO:1 or fragments thereof, where the cells contain transcriptional control DNA sequences, preferably other than human IL-1RP1 transcriptional control sequences, where the transcriptional control sequences control transcription of DNA encoding a polypeptide with the amino acid sequence according to SEQ ID NO:1 or fragments thereof.

In yet another aspect of the present invention there are provided assay methods and kits comprising the components necessary to detect above-normal expression of polynucleotides encoding a polypeptide comprising an amino acid sequence as set forth in SEQ ID NO:1, or polypeptides comprising an amino acid sequence set forth in SEQ ID NO:1, or fragments thereof, in body tissue samples derived from a patient, such kits comprising e.g., antibodies that bind to a polypeptide comprising an amino acid sequence set forth in SEQ ID NO:1, or to fragments thereof, or oligonucleotide probes that hybridize with polynucleotides of the invention. In a preferred embodiment, such kits also comprise instructions detailing the procedures by which the kit components are to be used.

In another aspect, the invention is directed to use of a polypeptide comprising an amino acid sequence set forth in SEQ ID NO:1 or fragment thereof, polynucleotide encoding such a polypeptide or a fragment thereof, or antibody that binds to said polypeptide comprising an amino acid sequence set forth in SEQ ID NO:1 or a fragment thereof in the manufacture of a medicament to treat diseases associated with host inflammatory or immune responses.

Another aspect is directed to pharmaceutical compositions comprising a polypeptide comprising or consisting of an amino acid sequence set forth in SEQ ID NO:1 or fragment thereof, a polynucleotide encoding such a polypeptide or a fragment thereof, or antibody that binds to such a polypeptide or a fragment thereof, in conjunction with a suitable pharmaceutical carrier, excipient or diluent, for the treatment of diseases associated with host inflammatory or immune responses.

In another aspect, the invention is directed to methods for the identification of molecules that can bind to a polypeptide comprising an amino acid sequence set forth in SEQ ID NO:1 and/or modulate the activity of a polypeptide comprising an amino acid sequence set forth in SEQ ID NO:1 or molecules that can bind to nucleic acid sequences that modulate the transcription or translation of a polynucleotide encoding a polypeptide comprising an amino acid sequence set forth in SEQ ID NO:1. Such methods are disclosed in, e.g., U.S. Pat. Nos. 5,541,070; 5,567,317; 5,593,853; 5,670, 326; 5,679,582; 5,856,083; 5,858,657; 5,866,341; 5,876, 946; 5,989,814; 6,010,861; 6,020,141; 6,030,779; and 6,043024, all of which are incorporated by reference herein in their entirety. Molecules identified by such methods also fall within the scope of the present invention.

In a related aspect, the invention is directed to methods for identification of a receptor to which the novel IL-1RP1 of the invention can bind. In this regard a number of technologies allow for the identification of receptors and binding proteins for molecules such as IL-1RP1 including but not limited to yeast-two-Hybrid analysis (S. Fields and O. Song, Nature, 1989 340:245–6) or techniques of expression cloning in mammalian cells involving using labeled or tagged ligands to find cells expressing a receptor after transfection of cDNA libraries.

In yet another aspect, the invention is directed to methods for the introduction of nucleic acids of the invention into one or more tissues of a subject in need of treatment with the result that one or more proteins encoded by the nucleic acids are expressed and or secreted by cells within the tissue.

Other objects, features, advantages and aspects of the present invention will become apparent to those of skill from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

FIG. 1A is a depiction of the full length cDNA sequence (SEQ ID No:2), encoding the novel IL-1RP1. Start and stop codons of the ORF are noted in bold underline; the sequence of the ORF contained within (SEQ ID NO:3) starts at nucleotide position no. 60 (atg) and ends at nucleotide position no. 516 i.e. before the stop codon (tag). FIG. 1B depicts the amino acid sequence (SEQ ID NO:1) of the novel IL-1RP1 which comprises 152 amino acids. The asterix (*) refers to the stop codon.

FIG. 2 is a depiction of the genomic DNA sequence (SEQ ID NO:4), encoding the novel interleukin-1 related polypeptide 1. The amino acids of the corresponding ORF are indicated. Also shown are restriction sites to allow for precise physical mapping of the genomic region.

FIG. 3 is an amino acid sequence comparison of the IL-1 family of proteins.

FIG. 4 depicts the expression of IL-1RP1 in different human tissues determined by RT-PCR.

FIG. 8 depicts the double stranded nucleotide sequence of IL-1RP1 cDNA.

DETAILED DESCRIPTION OF THE INVENTION

Figure 5:
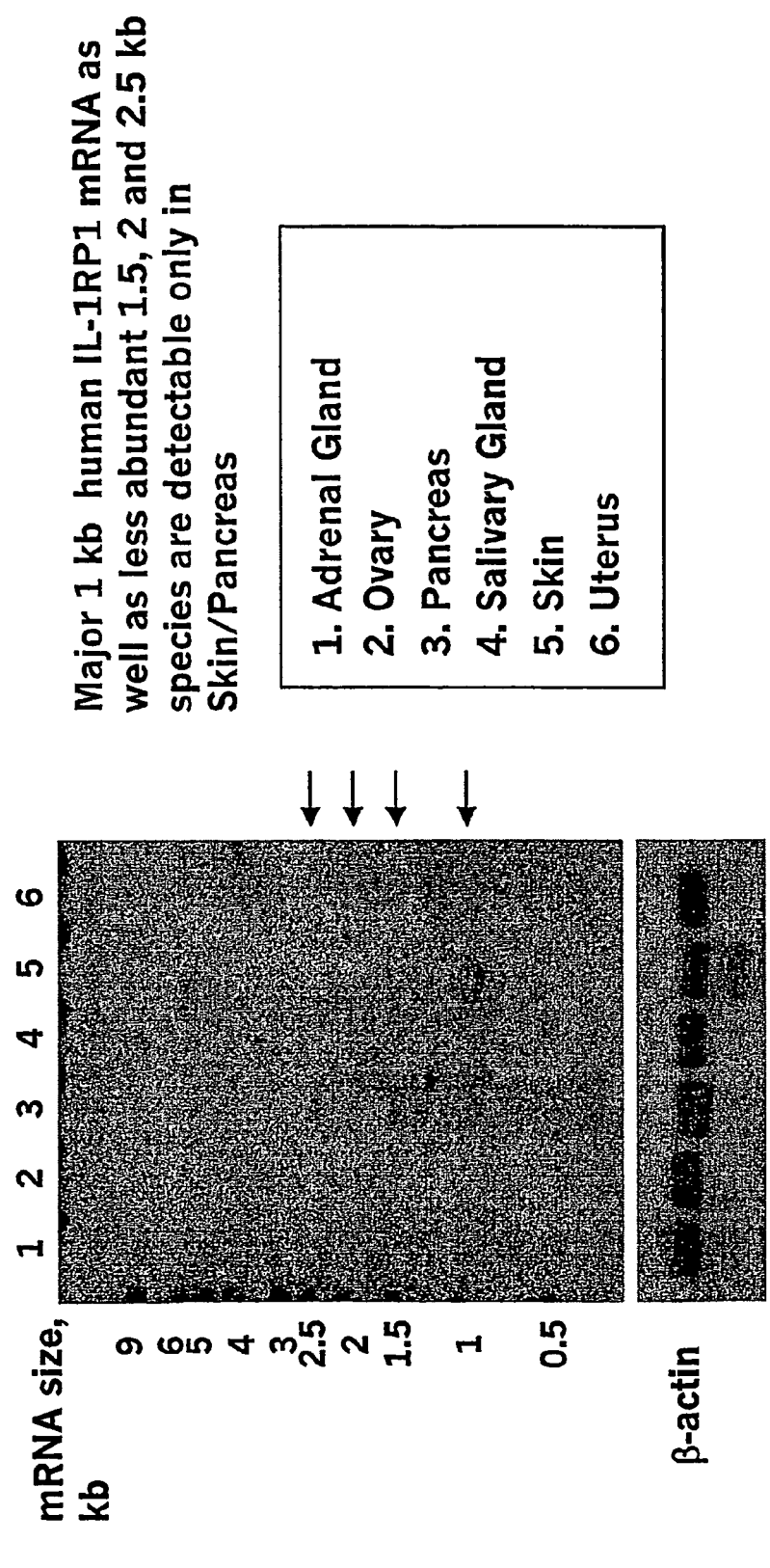
FIG. 5 depicts results of Northern blot analysis of human IL-1RP1 mRNA expression in various tissues.
Figure 6:
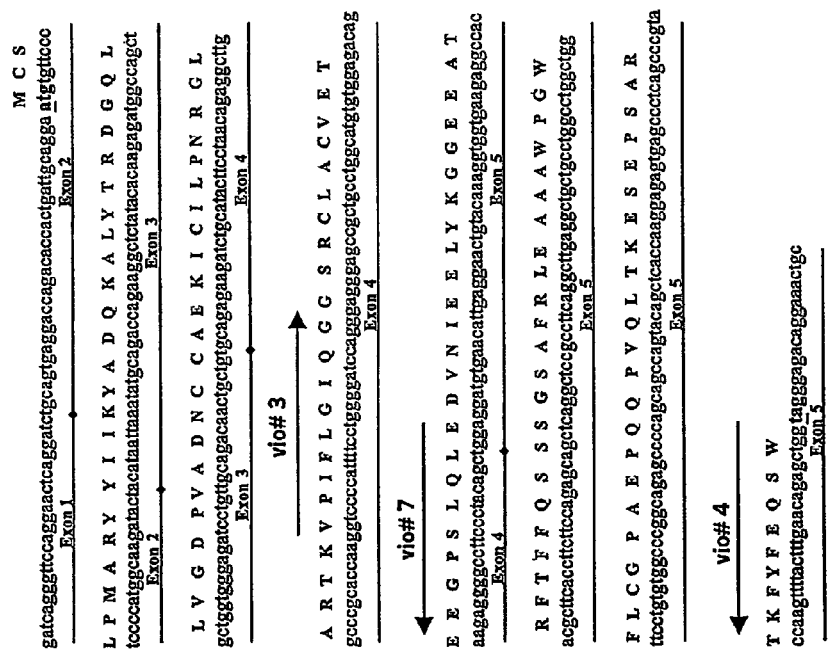
FIG. 6 depicts the primary sequence of IL-1RP1.

All patent applications, patents and literature references cited herein are hereby incorporated by reference in their entirety.

In practicing the present invention, many conventional techniques in molecular biology, microbiology, and recombinant DNA are used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985, (Hames and Higgins); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian Cells, 1987 (J. H. Miller and M. P. Calos eds., Cold Spring Harbor Laboratory); and Methods in Enzymology Vol. 154 and Vol. 155 (Wu and Grossman, and Wu, eds., respectively).

In its broadest sense, the term "substantially similar", when used herein with respect to a nucleotide sequence, means a nucleotide sequence corresponding to a reference nucleotide sequence, wherein the corresponding sequence encodes a polypeptide having substantially the same structure and function as the polypeptide encoded by the reference nucleotide sequence, e.g. where only changes in amino acids not affecting the polypeptide function occur. Desirably the substantially similar nucleotide sequence encodes the polypeptide encoded by the reference nucleotide sequence. The percentage of identity between the substantially similar nucleotide sequence and the reference nucleotide sequence desirably is at least 80%, more desirably at least 85%, preferably at least 90%, more preferably at least 95%, still more preferably at least 99%. Sequence comparisons are carried out using a Smith-Waterman sequence alignment algorithm (see e.g. Waterman, M. S. Introduction to Computational Biology: Maps, sequences and genomes. Chapman & Hall. London: 1995. ISBN 0-412-99391-0, or at http://www-hto.usc.edu/software/seqaln /index.html). The localS program, version 1.16, is used with following parameters: match: 1, mismatch penalty: 0.33, open-gap penalty: 2, extended-gap penalty: 2.

A nucleotide sequence "substantially similar" to reference nucleotide sequence hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C., yet still encodes a functionally equivalent gene product.

"Elevated transcription of mRNA" refers to a greater amount of messenger RNA transcribed from the natural endogenous human gene encoding the novel polypeptide of the present invention present in an appropriate tissue or cell of an individual suffering from a condition associated with host inflammatory or immune response in a larger amount, in particular at least about twice, preferably at least about five times, more preferably at least about ten times, most preferably at least about 100 times the amount of mRNA found in corresponding tissues in humans who do not suffer from such a condition. Such elevated level of mRNA may eventually lead to increased levels of protein translated from such mRNA in an individual suffering from a condition associated with host inflammatory or immune response as compared with a healthy individual.

A "host cell," as used herein, refers to a prokaryotic or eukaryotic cell that contains heterologous DNA that has been introduced into the cell by any means, e.g., electroporation, calcium phosphate precipitation, microinjection, transformation, viral infection, and the like.

"eterologous" as used herein means "of different natural origin" or represents a non-natural state. For example, if a host cell is transformed with a DNA or gene derived from another organism, particularly from another species, that gene is heterologous with respect to that host cell and also with respect to descendants of the host cell which carry that gene. Similarly, heterologous refers to a nucleotide sequence derived from and inserted into the same natural, original cell type, but which is present in a non-natural state, e.g. a different copy number, or under the control of different regulatory elements.

A "vector" molecule is a nucleic acid molecule into which heterologous nucleic acid may be inserted which can then be introduced into an appropriate host cell. Vectors preferably have one or more origin of replication, and one or more site into which the recombinant DNA can be inserted. Vectors often have convenient means by which cells with vectors can be selected from those without, e.g., they encode drug resistance genes. Common vectors include plasmids, viral genomes, and (primarily in yeast and bacteria) "artificial chromosomes."

"Plasmids" generally are designated herein by a lower case p preceded and/or followed by capital letters and/or numbers, in accordance with standard naming conventions that are familiar to those of skill in the art. Starting plasmids disclosed herein are either commercially available, publicly available on an unrestricted basis, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated, even if subsequently reintroduced into the natural system. Such polynucleotides could be part of a vector and/or such polynucleotides or polypeptides could be part of a composition, and still be isolated in that such vector or composition is not part of its natural environment.

As used herein, the term "transcriptional control sequence" refers to DNA sequences, such as initiator sequences, enhancer sequences, and promoter sequences, which induce, repress, or otherwise control the transcription of protein encoding nucleic acid sequences to which they are operably linked.

As used herein, "human transcriptional control sequences" are any of those transcriptional control sequences normally found associated with the human gene encoding the novel interleukin-1 related polypeptide of the present invention as it is found in the respective human chromosome.

As used herein, "non-human transcriptional control sequence" is any transcriptional control sequence not found in the human genome.

The term "polypeptide" is used interchangeably herein with the terms "polypeptides" and "protein(s)".

As used herein, a "chemical derivative" of a polypeptide of the invention is a polypeptide of the invention that contains additional chemical moieties not normally a part of the molecule. Such moieties may improve the molecule's solubility, absorption, biological half-life, etc. The moieties may alternatively decrease the toxicity of the molecule, eliminate or attenuate any undesirable side effect of the molecule, etc. Moieties capable of mediating such effects are disclosed, for example, in Remington's Pharmaceutical Sciences, 16th ed., Mack Publishing Co., Easton, Pa. (1980).

The invention generally relates to a novel nucleotide sequence which uniquely encodes a novel interleukin. The new gene encodes a polypeptide designated herein as interleukin-1 related polypeptide, or IL-1RP1, belonging to the interleukin-1 cytokine family, as will be outlined in detail herein.

In order to determine if additional members of the IL-1 family of polypeptides exist in the human genome, in-house and public human genomic databases are searched with the human IL-1β and IL-1H1 peptide sequences. IL-1H1 is an IL-1 related molecule that was recently shown to be constitutively expressed only in placenta and squamous epithelium of esophagus, and could be induced in vitro in keratinocytes. Using these two sequences as a bait and tBlastN program one novel sequence, not previously reported, is found corresponding to a certain clone of the in-house database. Translation of this genomic sequence shows 33% identity and 52% similarity to IL-1H1. This sequence is then used to find additional overlapping genomic sequences using BlastN thereby identifying a large segment of genomic DNA from the public database. Approximately 1 kb of genomic sequence flanking the sequence of the in-house database is translated in all six reading frames and compared by ClustalW to IL-1H1 and IL-1β peptide sequences. An additional sequence of 127 nucleotides is found. Based on identified primary sequence PCR primers are designed to amplify the coding region from fetal human small intestine Marathon® cDNA (Clonetech, Palo Alto, Calif.) and the sequence is found to be identical with that predicted by the genomic region. Finally a 5' RACE is used to identify the 5' end of the cDNA. The sequence of the complete coding region for IL-1RP1 is shown in FIG. 1. Similar to all of the IL-1 family members except for IL-1RA, IL-1RP1 does not contain a hydrophobic secretion signal. Thus IL-1RP1 is likely produced as an intracellular protein and released upon cell damage as are IL-1α and the intracellular forms of IL-RA to gain its biological function.

The full length cDNA for IL-1RP1 predicts a protein of 152 amino acids. The identity profile of the family of IL-1 related molecules is shown in the following Table 1.

outlined above, IL-1RP1 is clearly a member of the IL-1 family since it is highly similar to other IL-1 proteins as discussed above. It also shares many similarities with the IL-1 family. The genomic sequences for IL-1RP1 is found on chromosome 2 on the same human genomic BAC clone as FILε and IL-1H1. To date all of the IL-1 related molecules are on the same portion of chromosome 2 suggesting a relatively recent evolutionary divergence. Finally, analysis of genomic sequences and cDNA sequences shows that the

TABLE 1

|        | IL1RP1 | IL-1RA | IL-1β | IL-1α | IL1H1 | IL1H2/v | FILδ/H3 | FILε | FILζ/H4 | IL-18 |
|--------|--------|--------|-------|-------|-------|---------|---------|------|---------|-------|
| IL1RP1 |        | 38     | 22    | 20    | 28    | 17      | 42      | 27   | 27      | 18    |
| IL-1RA |        |        | 31    | 20    | 29    | 26      | 21      | 23   | 21      | 21    |
| IL-1β  |        |        |       | 24    | 20    | 32      | 32      | 27   | 24      | 17    |
| IL-1   |        |        |       |       | 25    | 26      | 20      | 23   | 21      | 21    |
| IL1H1  |        |        |       |       |       | 26      | 29      | 60   | 30      | 24    |
| IL-1H2/v |      |        |       |       |       |         | 21      | 46   | 44      | 21    |
| FILδ/H3 |       |        |       |       |       |         |         | 31   | 35      | 27    |
| FILε   |        |        |       |       |       |         |         |      | 36      | 21    |
| FILζ/H4 |       |        |       |       |       |         |         |      |         | 21    |
| IL-18  |        |        |       |       |       |         |         |      |         |       |

Table 1 shows the percentage of identity of IL-1 family of proteins, including the novel IL-1RP1. Note that FILζ and IL1H4 are listed as the same gene as they are 88% identical and differ only at the very amino and carboxyl terminal ends and thus likely represent alternate spliced forms of the same gene. Also IL-1H2 and FILv as well as IL-1H3 and FILδ are listed as the same gene. The mature forms of IL-1α, IL-1β, IL-1RA and IL-18 are used for comparison. Percent identifies were determined using a global alignment as described by Myers and Miller, CABIOS 1989 4:11–17 and using a BLOSUM50 scoring matrix with gap penalties of −12/−2.

The predicted IL-1RP1 peptide is most homologous to IL-1H3/FILδ and IL-1RA, being 42% and 38% identical, respectively.

As thus being qualified as a member of the IL-1 polypeptide family, the novel polypeptide IL-1RP1 will have similar physiological functions. It is likely to be involved in inflammation or host immune response due to its similarity to the IL-1 related polypeptides of known function, all of which have major impact in human disease. The sequence and predicted structure of IL-1RP1 will be useful for designing antiinflammatory agents either through the use of small molecules or proteins (e.g. antibodies) directed against it or its receptor. In addition, protein derived from the IL-1RP1 sequence may also be used as a therapeutic to modify host immune or inflammatory responses.

To determine the expression pattern of the novel polypeptide, a panel of cDNAs from a variety of human tissues is subjected to PCR analysis using PCR primers that could identify an IL-1RP1 transcript. PCR primers are chosen that are present on separate exons of the predicted IL-1RP1 gene so that PCR products from a transcribed, processed mRNA can readily be distinguished from any originating genomic DNA. As a result, IL-1RP1 is differentially expressed in human tissues, being detectable in brain, heart, liver, lung, stomach, testis, placenta, prostate and skin. Most notably IL-1RP1 is highly expressed in skin. Thus IL-1RP represents a transcribed gene. Further its constitutive expression is very high in skin suggesting it may play a role in cutaneous inflammatory responses. See FIG. 4.

Therefore, in one aspect, the present invention relates to a novel interleukin-1 related polypeptide (IL-1RP1). As intron exon organization for IL-1RP1 is almost identical to IL-1RA and FILδ. These observations are consistent with the assumption that all are derived from the same ancestral gene.

The present invention relates to an isolated polypeptide comprising the amino acid sequence set forth in SEQ ID NO:1. Such a polypeptide may for example be a fusion protein including the amino acid sequence of the novel interleukin-1 related polypeptide 1. In another aspect the present invention relates to an isolated polypeptide consisting of the amino acid sequence set forth in SEQ ID NO:1, which is, in particular, the novel IL-1RP1.

The invention includes nucleic acid or nucleotide molecules, preferably DNA molecules, in particular encoding the novel IL-1RP1. Preferably, an isolated nucleic acid molecule, preferably a DNA molecule, of the present invention encodes a polypeptide comprising the amino acid sequence set forth in SEQ ID NO:1. Likewise preferred is an isolated nucleic acid molecule, preferably a DNA molecule, encoding a polypeptide consisting of the amino acid sequence set forth in SEQ ID NO:1. Such a nucleic acid or nucleotide, in particular such a DNA molecule, preferably comprises a nucleotide sequence selected from the group consisting of (1) the nucleotide sequence as set forth in SEQ ID NO:2, which is the complete cDNA sequence encoding the polypeptide consisting of the amino acid sequence set forth in SEQ ID NO:1; (2) the nucleotide sequence set forth in SEQ ID NO:3, which corresponds to the open reading frame of the cDNA sequence set forth in SEQ ID NO:2; (3) a nucleotide sequence capable of hybridizing under high stringency conditions to a nucleotide sequence set forth in SEQ ID NO:3; and (4) the nucleotide sequence set forth in SEQ ID NO:4, which corresponds to the endogenous human genomic DNA encoding the polypeptide consisting of the amino acid sequence set forth in SEQ ID NO:1. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). Suitable ranges of such stringency conditions for nucleic acids of varying compositions are described in Krause and Aaronson (1991), Methods in Enzymology, 200:546–556 in addition to Maniatis et al., cited above.

These nucleic acid molecules may act as target gene antisense molecules, useful, for example, in target gene regulation and/or as antisense primers in amplification reactions of target gene nucleic acid sequences. Further, such sequences may be used as part of ribozyme and/or triple helix sequences, also useful for target gene regulation. Still further, such molecules may be used as components of diagnostic methods whereby the presence of an allele causing diseases associated with host inflammatory or immune response may be detected.

The invention also encompasses (a) vectors that contain at least a fragment of any of the foregoing nucleotide sequences and/or their complements (i.e., antisense); (b) vector molecules, preferably vector molecules comprising transcriptional control sequences, in particular expression vectors, which contain any of the foregoing coding sequences operatively associated with a regulatory element that directs the expression of the coding sequences; and (c) genetically engineered host cells that contain a vector molecule as mentioned herein or at least a fragment of any of the foregoing nucleotide sequences operatively associated with a regulatory element that directs the expression of the coding sequences in the host cell. As used herein, regulatory elements include, but are not limited to, inducible and non-inducible promoters, enhancers, operators and other elements known to those skilled in the art that drive and regulate expression. Preferably, host cells can be vertebrate host cells, preferably mammalian host cells, like human cells or rodent cells, such as CHO or BHK cells. Likewise preferred, host cells can be bacterial host cells, in particular *E.coli* cells.

Particularly preferred is a host cell, in particular of the above described type, which can be propagated in vitro and which is capable upon growth in culture of producing an IL-1RP1 polypeptide, in particular a polypeptide comprising or consisting of an amino acid sequence set forth in SEQ ID NO:1, wherein said cell comprises at least one transcriptional control sequence that is not a transcriptional control sequence of the natural endogenous human gene encoding said polypeptide, wherein said one or more transcriptional control sequences control transcription of a DNA encoding said polypeptide.

The invention includes fragments of any of the nucleic acid sequences disclosed herein. Fragments of the nucleic acid sequences encoding the novel IL-1RP1 polypeptide may be used as a hybridization probe for a cDNA library to isolate the full length gene and to isolate other genes which have a high sequence similarity to the IL-1RP1 gene or similar biological activity. Probes of this type preferably have at least about 30 bases and may contain, for example, from about 30 to about 50 bases, about 50 to about 100 bases, about 100 to about 200 bases, or more than 200 bases. The probe may also be used to identify a cDNA clone corresponding to a full length transcript and a genomic clone or clones that contain the complete IL-1RP1 gene including regulatory and promoter regions, exons, and introns. An example of a screen comprises isolating the coding region of the IL-1RP1 gene by using the known DNA sequence to synthesize an oligonucleotide probe. Labeled oligonucleotides having a sequence complementary to that of the gene of the present invention are used to screen a library of human cDNA, genomic DNA or mRNA to determine to which members of the library the probe hybridizes.

In addition to the gene sequences described above, homologs of such sequences, as may, for example, be present in other species, may be identified and may be readily isolated, without undue experimentation, by molecular biological techniques well known in the art. Further, there may exist genes at other genetic loci within the genome that encode proteins which have extensive homology to one or more domains of such gene products. These genes may also be identified via similar techniques.

For example, the isolated nucleotide sequence of the present invention encoding the novel IL-1RP1 polypeptide may be labeled and used to screen a cDNA library constructed from mRNA obtained from the organism of interest. Hybridization conditions will be of a lower stringency when the cDNA library was derived from an organism different from the type of organism from which the labeled sequence was derived. Alternatively, the labeled fragment may be used to screen a genomic library derived from the organism of interest, again, using appropriately stringent conditions. Such low stringency conditions will be well known to those of skill in the art, and will vary predictably depending on the specific organisms from which the library and the labeled sequences are derived. For guidance regarding such conditions see, for example, Sambrook et al. cited above.

Further, a previously unknown differentially expressed gene-type sequence may be isolated by performing PCR using two degenerate oligonucleotide primer pools designed on the basis of amino acid sequences within the gene of interest. The template for the reaction may be cDNA obtained by reverse transcription of mRNA prepared from human or non-human cell lines or tissue known or suspected to express a differentially expressed gene allele.

The PCR product may be subcloned and sequenced to ensure that the amplified sequences represent the sequences of a differentially expressed gene-like nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to screen a genomic library.

PCR technology may also be utilized to isolate full length cDNA sequences. For example, RNA may be isolated, following standard proceduies, from an appropriate cellular or tissue source. A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies which may be used, see e.g., Sambrook et al., 1989, supra.

In cases where the gene identified is the normal, or wild type, gene, this gene may be used to isolate mutant alleles of the gene. Such an isolation is preferable in processes and disorders which are known or suspected to have a genetic basis. Mutant alleles may be isolated from individuals either known or suspected to have a genotype which contributes to disease symptoms related to inflammation or immune response. Mutant alleles and mutant allele products may then be utilized in the diagnostic assay systems described below.

A cDNA of the mutant gene may be isolated, for example, by using PCR, a technique which is well known to those of skill in the art. In this case, the first cDNA strand may be synthesized by hybridizing an oligo-dT oligonucleotide to mRNA isolated from tissue known or suspected to be expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof may then be labeled and used as a probed to identify the corresponding mutant allele in the library. The clone containing this gene may then be purified through methods routinely practiced in the art, and subjected to sequence analysis as described above.

Additionally, an expression library can be constructed utilizing DNA isolated from or cDNA synthesized from a tissue known to or suspected of expressing the gene of interest in an individual suspected of or known to carry the mutant allele. In this manner, gene products made by the putatively mutant tissue may be expressed and screened using standard antibody screening techniques in conjunction with antibodies raised against the normal gene product, as described, below. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described above.

The present invention includes those proteins encoded by nucleotide sequences set forth in any of SEQ ID NOs:2, 3 or 4, in particular, a polypeptide that is or includes the amino acid sequence set out in SEQ ID NO:1, or fragments thereof.

Furthermore, the present invention includes proteins that represent functionally equivalent gene products. Such an equivalent differentially expressed gene product may contain deletions, additions or substitutions of amino acid residues within the amino acid sequence encoded by the differentially expressed gene sequences described, above, but which result in a silent change, thus producing a functionally equivalent differentially expressed gene product. Amino acid substitutions may be made on the basis of similarity in polarity, charge, solubility, hydrophobicity, hydrophilicity, and/or the amphipathic. nature of the residues involved.

For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent," as utilized herein, may refer to a protein or polypeptide capable of exhibiting a substantially similar in vivo or in vitro activity as the endogenous differentially expressed gene products encoded by the differentially expressed gene sequences described above. "Functionally equivalent" may also refer to proteins or polypeptides capable of interacting with other cellular or extracellular molecules in a manner substantially similar to the way in which the corresponding portion of the endogenous differentially expressed gene product would. For example, a "functionally equivalent" peptide would be able, in an immunoassay, to diminish the binding of an antibody to the corresponding peptide (i.e., the peptide the amino acid sequence of which was modified to achieve the "functionally equivalent" peptide) of the endogenous protein, or to the endogenous protein itself, where the antibody was raised against the corresponding peptide of the endogenous protein. An equimolar concentration of the functionally equivalent peptide will diminish the aforesaid binding of the corresponding peptide by at least about 5%, preferably between about 5% and 10%, more preferably between about 10% and 25%, even more preferably between about 25% and 50%, and most preferably between about 40% and 50%.

The polypeptides of the present invention may be produced by recombinant DNA technology using techniques well known in the art. Therefore, there is provided a method of producing a polypeptide of the present invention, which method comprises culturing a host cell having incorporated therein an expression vector containing an exogenously-derived polynucleotide encoding a polypeptide comprising an amino acid sequence as set forth in SEQ ID NO:1 under conditions sufficient for expression of the polypeptide in the host cell, thereby causing the production of the expressed polypeptide. Optionally, said method further comprises recovering the polypeptide produced by said cell. In a preferred embodiment of such a method,. said exogenously-derived polynucleotide encodes a polypeptide consisting of an amino acid sequence set forth in SEQ ID NO:1. Preferably, said exogenously-derived polynucleotide comprises the nucleotide sequence as set forth in any of SEQ ID NO:2, SEQ ID NO:3 or SEQ ID NO:4. In case of using the nucleotide sequence set forth in SEQ ID NO:2, i.e. the open reading frame, the sequence, when inserted into a vector, may be followed by one or more appropriate translation stop codons, preferably by the natural endogenous stop codon as shown in FIG. 1.

Thus, methods for preparing the polypeptides and peptides of the invention by expressing nucleic acid encoding respective nucleotide sequences are described herein. Methods that are well known to those skilled in the art can be used to construct expression vectors containing protein-coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, supra, and Ausubel et al., 1989, supra. Alternatively, RNA capable of encoding differentially expressed gene protein sequences may be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems may be utilized to express the differentially expressed gene coding sequences of the invention. Such host-expression systems represent vehicles by which the coding sequences of interest may be produced and subsequently purified, but also represent cells which may, when transformed or transfected with the appropriate nucleotide coding sequences, exhibit the differentially expressed gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed gene protein coding sequences; yeast (e.g. *Saccharomyces, Pichia*) transformed with recombinant yeast expression vectors containing the differentially expressed gene protein coding sequences; insect cell systems infected or transfected with recombinant virus expression vectors (e.g., baculovirus) containing the differentially expressed gene protein coding sequences; plant cell systems infected with recombinant virus expression vectors (e.g., cauliflower mosaic virus, CaMV; tobacco mosaic virus, TM4V) or transformed with recombinant vectors, including plasmids, (e.g., Ti plasmid) containing protein coding sequences; or mammalian cell systems (e.g. COS, CHO, BHK, 293, 3T3) harboring recombinant expression constructs containing promoters derived from the genome of mammalian cells (e.g., metallothioneine promoter) or from mammalian viruses (e.g., the adenovirus late promoter; the vaccinia virus 75K promoter, or the CMV promoter).

Expression of the interleukin-1 related polypeptide 1 of the present invention by a cell from an IL-1RP1-encoding gene that is native to the cell can also be performed. Methods for such expression are detailed in, e.g., U.S. Pat. Nos. 5,641,670; 5,733,761; 5,968,502; and 5,994,127, all of which are expressly incorporated by reference herein in their entirety. Cells that have been induced to express IL-1RP1 by the methods of any of U.S. Pat. Nos. 5,641,670; 5,733,761; 5,968,502; and 5,994,127 can be implanted into a desired tissue in a living animal in order to increase the local concentration of IL-1RP1 in the tissue.

In bacterial systems, a number of expression vectors may be advantageously selected depending upon the use intended for the protein being expressed. For example, when a large quantity of such a protein is to be produced, for the generation of antibodies or to screen peptide libraries, for example, vectors which direct the expression of high levels of fusion protein products that are readily purified may be desirable. In this respect, fusion proteins comprising hexahistidine tags may be used (Sisk et alk, 1994: J. Virol 68: 766–775) as provided by a number of vendors (e.g. Qiagen, Valencia, Calif.). Such vectors include, but are not limited, to the *E. coli* expression vector pUR278 (Ruther et al., 1983, EMBO J. 2:1791), in which the protein-encoding sequence may be ligated individually into the vector in frame with the lac Z coding region so that a fusion protein is produced; pIN vectors Inouye & Inouye, 1985, Nucleic Acids Res. 13:3101–3109; Van Heeke & Schuster, 1989, J. Biol. Chem. 264:5503–5509); and the like. pGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

Promoter regions can be selected from any desired gene using vectors that contain a reporter transcription unit lacking a promoter region, such as a chloramphenicol acetyl transferase ("CAT"), or the luciferase transcription unit, downstream of restriction site or sites for introducing a candidate promoter fragment; i.e., a fragment that may contain a promoter. For example, introduction into the vector of a promoter-containing fragment at the restriction site upstream of the CAT gene engenders production of CAT activity, which can be detected by standard CAT assays. Vectors suitable to this end are well known and readily available. Two such vectors are pKK232-8 and pCM7. Thus, promoters for expression of polynucleotides of the present invention include not only well-known and readily available promoters, but also promoters that readily may be obtained by the foregoing technique, using a reporter gene.

Among known bacterial promoters suitable for expression of polynucleotides and polypeptides in accordance with the present invention are the *E. coli* lacI and lacZ promoters, the T3 and T7 promoters, the T5 tac promoter, the lambda PR, PL promoters and the trp promoter. Among known eukaryotic promoters suitable in this regard are the CMV immediate early promoter, the HSV thymidine kinase promoter, the early and late SV40 promoters, the promoters of retroviral LTRs, such as those of the Rous sarcoma virus ("RSV"), and metallothionein promoters, such as the mouse metallothionein-I promoter.

In an insect system, *Autographa californica* nuclear polyhedrosis virus (AcNPV) is one of several insect systems that can be used as a vector to express foreign genes. The virus grows in Spodoptera frugiperda cells. The coding sequence may be cloned individually into non-essential regions (for example the polyhedrin gene) of the virus and placed under control of an AcNPV promoter (for example the polyhedrin promoter). Successful insertion of the coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed. (E.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the desired protein in infected hosts. (E.g., See Logan & Shenk, 1984, Proc. Natl. Acad. Sci. USA 81:3655–3659). Specific initiation signals may also be required for efficient translation of inserted gene coding sequences. These signals include the ATG initiation codon and adjacent sequences. In cases where an entire gene, including its own initiation codon and adjacent sequences, is inserted into the appropriate expression vector, no additional translational control signals may be needed. However, in cases where only a portion of the gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544). Other common systems are based on SV40, retrovirus or adeno-associated virus. Selection of appropriate vectors and promoters for expression in a host cell is a well-known procedure and the requisite techniques for expression vector construction, introduction of the vector into the host and expression in the host per se are routine skills in the art. Generally, recombinant expression vectors will include origins of replication, a promoter derived from a highly expressed gene to direct transcription of a downstream structural sequence, and a selectable marker to permit isolation of vector containing cells after exposure to the vector.

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the differentially expressed gene protein may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines that express the differentially expressed gene protein. Such engineered cell lines may be particularly useful in screening and evaluation of compounds that affect the endogenous activity of the expressed protein.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026),. and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

An alternative fusion protein system allows for the ready purification of non-denatured fusion proteins expressed in human cell lines (Janknecht, et al., 1991, Proc. Natl. Acad. Sci. USA 88: 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

When used as a component in assay systems such as those described below, a protein of the present invention may be labeled, either directly or indirectly, to facilitate detection of a complex formed between the protein and a test substance. Any of a variety of suitable labeling systems may be used including but not limited to radioisotopes such as $^{125}I$; enzyme labeling systems that generate a detectable calorimetric signal or light when exposed to substrate; and fluorescent labels.

Where recombinant DNA technology is used to produce a protein of the present invention for such assay systems, it may be advantageous to engineer fusion proteins that can facilitate labeling, immobilization, detection and/or isolation Indirect labeling involves the use of a protein, such as a labeled antibody, which specifically binds to a polypeptide of the present invention. Such antibodies include but are not limited to polyclonal, monoclonal, chimeric, single chain, Fab fragments and fragments produced by a Fab expression library.

In another embodiment, nucleic acids comprising a sequence encoding an IL-1RP1protein or functional derivative thereof are administered to promote normal immune system function, by way of gene therapy. Gene therapy refers to therapy performed by the administration of a nucleic acid to a subject. In this embodiment of the invention, the nucleic acid produces its encoded protein that mediates a therapeutic effect by promoting normal immune system function.

Any of the methods for gene therapy available in the art can be used according to the present invention. Exemplary methods are described below.

In a preferred aspect, the therapeutic comprises an IL-1RP1 nucleic acid that is part of an expression vector that expresses an IL-1RP1 protein or fragment or chimeric protein thereof in a suitable host. In particular, such a nucleic acid has a promoter operably linked to the IL-1RP1 coding region, said promoter being inducible or constitutive, and, optionally, tissue-specific. In another particular embodiment, a nucleic acid molecule is used in which the IL-1RP1 coding sequences and any other desired sequences are flanked by regions that promote homologous recombination at a desired site in the genome, thus providing for intrachromosomal expression of the IL-1RP1 nucleic acid (Koller and Smithies, 1989, Proc. Natl. Acad. Sci. USA 86:8932–8935; Zijlstra et al., 1989, Nature 342:435–438).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see, e.g., U.S. Pat. No. 4,980,286 and others mentioned infra), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., U.S. Pat. Nos. 5,166,320; 5,728,399; 5,874,297; and 6,030,954, all of which are incorporated by reference herein in their entirety) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188; and WO 93/20221). Alternatively, the nucleic acid can be introduced intracellularly and incorporated within host cell DNA for expression, by homologous recombination (see, e.g., U.S. Pat. Nos. 5,413,923; 5,416,260; and 5,574,205; and Zijlstra et al., 1989, Nature 342:435–438).

In a specific embodiment, a viral vector that contains the IL-1RP1 nucleic acid is used. For example, a retroviral vector can be used (see, e.g., U.S. Pat. Nos. 5,219,740; 5,604,090; and 5,834,182). These retroviral vectors have been modified to delete retroviral sequences that are not necessary for packaging of the viral genome and integration into host cell DNA. The IL-1RP1 nucleic acid to be used in gene therapy is cloned into the vector, which facilitates delivery of the gene into a patient.

Adenoviruses are other viral vectors that can be used in gene therapy. Adenoviruses are especially attractive vehicles for delivering genes to respiratory epithelia Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Methods for conducting adenovirus-based gene therapy are described in, e.g., U.S. Pat. Nos. 5,824,544; 5,868,040; 5,871,722; 5,880,102; 5,882,877; 5,885,808; 5,932,210; 5,981,225; 5,994,106; 5,994,132; 5,994,134; 6,001,557; and 6,033,8843, all of which are incorporated by reference herein in their entirety.

Adeno-associated virus (AAV) has also been proposed for use in gene therapy. Methods for producing and utilizing AAV are described, e.g., in U.S. Pat. Nos. 5,173,414; 5,252,479; 5,552,311; 5,658,785; 5,763,416; 5,773,289; 5,843,742; 5,869,040; 5,942,496; and 5,948,675, all of which are incorporated by reference herein in their entirety.

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, an IL-1RP1 nucleic acid is introduced into the cells such that it is expressible by the cells or their progeny, and the recombinant cells are then administered in vivo for therapeutic effect. In a specific embodiment, stem or progenitor cells are used. Any stem-and/or progenitor cells that can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (see, e.g., WO 94/08598), and neural stem cells (Stemple and Anderson, 1992, Cell 71:973–985).

Epithelial stem cells (ESCs) or keratinocytes can be obtained from tissues such as the skin and the lining of the gut by known procedures (Rheinwald, 1980, Meth. Cell Bio. 21A:229). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Pittelkow and Scott, 1986, Mayo Clinic Proc. 61:771). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique that provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., 1984, J. Clin. Invest. 73:1377–1384). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., 1977, J. Cell Physiol. 91:335) or Witlock-Witte culture techniques (Witlock and Witte, 1982, Proc. Natl. Acad. Sci. USA 79:3608–3612).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

A further embodiment of the present invention relates to a purified antibody or a fragment thereof which specifically binds to a polypeptide that comprises the amino acid sequence set forth in SEQ ID NO:1 or to a fragment of said polypeptide. A preferred embodiment relates to a fragment of such an antibody, which fragment is an Fab or F(ab')$_2$ fragment. In particular, the antibody can be a polyclonal antibody or a monoclonal antibody.

Described herein are methods for the production of antibodies capable of specifically recognizing one or more differentially expressed gene epitopes. Such antibodies may include, but are not limited to polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a fingerprint, target, gene in a biological sample, or, alternatively, as a method for the inhibition of abnormal target gene activity. Thus, such antibodies may be utilized as part of cardiovascular disease treatment methods, and/or may be used as part of diagnostic techniques whereby patients may be tested for abnormal levels of the IL-1RPI polypeptide, or for the presence of abnormal forms of the IL-1RP1 polypeptide.

For the production of antibodies to the IL-1RP1 polypeptide, various host animals may be immunized by injection with the IL-1RP1 polypeptide, or a portion thereof. Such host animals may include but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and Corynebacterium parvum.

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, may be immunized by injection with the IL-1RP1 polypeptide, or a portion thereof, supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to the hybridoma technique of Kohler and Milstein, (1975, Nature 256:495497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable or hypervariable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce differentially expressed gene-single chain antibodies. Single chain antibodies are formed by linking the heavy and light chain fragments of the Fv region via an amino acid bridge, resulting in a single chain polypeptide.

Most preferably, techniques useful for the production of "humanized antibodies" can be adapted to produce antibodies to the polypeptides, fragments, derivatives, and functional equivalents disclosed herein. Such techniques are disclosed in U.S. Pat. Nos. 5,932,448; 5,693,762; 5,693,761; 5,585,089; 5,530,101; 5,910,771; 5,569,825; 5,625,126; 5,633,425; 5,789,650; 5,545,580; 5,661,016; and 5,770,429, the disclosures of all of which are incorporated by reference herein in their entirety.

Antibody fragments that recognize specific epitopes may be generated by known techniques. For example, such fragments include but are not limited to: the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed (Huse et al., 1989, Science, 246:1275–1281) to allow rapid and easy identification of monoclonal Fab fragments with the desired specificity.

An antibody of the present invention can be preferably used in a method for the diagnosis of a condition associated with host inflammatory or immune response in a human which comprises: measuring the amount of a polypeptide comprising the amino acid sequence set forth in SEQ ID NO:1, or fragments thereof, in an appropriate tissue or cell from a human suffering from a condition associated with host inflammatory or immune response, wherein the presence of an elevated amount of said polypeptide or fragments thereof, relative to the amount of said polypeptide or fragments thereof in the respective tissue from a human not suffering from a condition associated with host inflammatory or immune response is diagnostic of said human's suffering from a condition associated with host inflammatory or immune response. Such a method forms a further embodiment of the present invention. Preferably, said detecting step comprises contacting said appropriate tissue or cell with an antibody which specifically binds to a polypeptide that comprises the amino acid sequence set forth in SEQ ID NO:1 or a fragment thereof and detecting specific binding of said antibody with a polypeptide in said appropriate tissue or cell, wherein detection of specific binding to a polypeptide indicates the presence of a polypeptide that comprises the amino acid sequence set forth in SEQ ID NO:1 or a fragment thereof.

Particularly preferred, for ease of detection, is the sandwich assay, of which a number of variations exist, all of which are intended to be encompassed by the present invention.

For example, in a typical forward assay, unlabeled antibody is immobilized on a solid substrate and the sample to be tested brought into contact with the bound molecule. After a suitable period of incubation, for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody that is specific for the IL-1RP1 polypeptide or a fragment thereof.

The most commonly used reporter molecules in this type of assay are either enzymes, fluorophore- or radionuclide-containing molecules. In the case of an enzyme immunoassay an enzyme is conjugated to the second antibody, usually by means of glutaraldehyde or periodate. As will be readily recognized, however, a wide variety of different ligation techniques exist, which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of IL-1RP1 which is present in the serum sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

This invention also relates to the use of polynucleotides of the present invention as diagnostic reagents. In particular, the invention relates to a method for the diagnosis of a condition associated with host inflammatory or immune response in a human which comprises: detecting elevated transcription of messenger RNA transcribed from the natural endogenous human gene encoding the polypeptide consisting of an amino acid sequence set forth in SEQ ID NO:1 in an appropriate tissue or cell from a human, wherein said elevated transcription is diagnostic of said human's suffering from the condition associated with host inflammatory or immune response. In particular, said natural endogenous human gene comprises the nucleotide sequence set forth in SEQ ID NO:4. In a preferred embodiment such a method comprises contacting a sample of said appropriate tissue or cell or contacting an isolated RNA or DNA molecule derived from that tissue or cell with an isolated nucleotide sequence of at least about 20 nucleotides in length that hybridizes under high stringency conditions with the isolated nucleotide sequence encoding a polypeptide consisting of an amino acid sequence set forth in SEQ ID NO:1.

Detection of a mutated form of the gene characterized by the polynucleotide of SEQ ID NO:4 which is associated with a dysfunction will provide a diagnostic tool that can add to, or define, a diagnosis of a disease, or susceptibility to a disease, which results from under-expression, over-expression or altered spatial or temporal expression of the gene. Individuals carrying mutations in the gene may be detected at the DNA level by a variety of techniques.

Nucleic acids, in particular mRNA, for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Hybridizing amplified DNA to labeled nucleotide sequences encoding the IL-1RP1 polypeptide of the present invention can identify point mutations. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing (e.g., Myers et al., Science (1985) 230:1242). Sequence changes at specific locations may also be revealed by nuclease protection assays, such as RNase and S1 protection or the chemical cleavage method (see Cotton et al., Proc Natl Acad Sci USA (1985) 85: 4397–4401). In another embodiment, an array of oligonucleotides probes comprising nucleotide sequence encoding the IL-1RP1 polypeptide of the present invention or fragments of such a nucleotide sequence can be constructed to conduct efficient screening of e.g., genetic mutations. Array technology methods are well known and have general applicability and can be used to address a variety of questions in molecular genetics including gene expression, genetic linkage, and genetic variability (see for example: M. Chee et al., Science, Vol 274, pp 610–613 (1996)).

The diagnostic assays offer a process for diagnosing or determining a susceptibility to disease through detection of mutation in the IL-1RP1 gene by the methods described. In addition, such diseases may be diagnosed by methods comprising determining from a sample derived from a subject an abnormally decreased or increased level of polypeptide or mRNA. Decreased or increased expression can be measured at the RNA level using any of the methods well known in the art for the quantitation of polynucleotides, such as, for example, nucleic acid amplification, for instance PCR, RT-PCR, RNase protection, Northern blotting and other hybridization methods. Assay techniques that can be used to determine levels of a protein, such as a polypeptide of the present invention, in a sample derived from a host are well known to those of skill in the art. Such assay methods include radioimmunoassays, competitive-binding assays, Western Blot analysis and ELISA assays.

Thus in another aspect, the present invention relates to a diagnostic kit which comprises:

(a) a polynucleotide of the present invention, preferably the nucleotide sequence of SEQ ID NO:2, 3 or 4, or a fragment thereof;

(b) a nucleotide sequence complementary to that of (a);

(c) a polypeptide of the present invention, preferably the polypeptide of SEQ ID NO:1 or a fragment thereof; or (d) an antibody to a polypeptide of the present invention, preferably to the polypeptide of SEQ ID NO:1.

It will be appreciated that in any such kit, (a), (b), (c) or (d) may comprise a substantial component. Such a kit will be of use in diagnosing a disease or susceptibility to a disease, particularly to a disease or condition associated with inflammation or immune response.

The nucleotide sequences of the present invention are also valuable for chromosome localization. The sequence is specifically targeted to, and can hybridize with, a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found in, for example, V. McKusick, Mendelian Inheritance in Man (available on-line through Johns Hopkins University Welch Medical Library). The relationship between genes and diseases that have been mapped to the same chromosomal region are then identified through linkage analysis (coinheritance of physically adjacent genes).

The differences in the cDNA or genomic sequence between affected and unaffected individuals can also be determined. If a mutation is observed in some or all of the affected individuals but not in any normal individuals, then the mutation is likely to be the causative agent of the disease.

An additional embodiment of the invention relates to the administration of a pharmaceutical composition, in conjunction with a pharmaceutically acceptable carrier, excipient or diluent, for any of the therapeutic effects discussed above. Such pharmaceutical compositions may consist of the interleukin-1 related polypeptide 1, antibodies to that polypeptide, mimetics, agonists, antagonists, or inhibitors of IL-1RP1 function. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions encompassed by the invention may be administered by any number of routes including, but not limited to, oral, intravenous, intramuscular, intra-articular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically acceptable carriers comprising excipients and auxiliaries that facilitate processing of the active compounds into preparations which can be used pharmaceutically. Further details on techniques for formulation and administration may be found in the latest edition of Remington's Pharmaceutical Sciences (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated m aqueous solutions, preferably in physiologically compatible buffers such as Hanks' solution, Ringer's solution, or physiologically buffered saline. Aqueous injection suspensions may contain substances that increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents that increase the solubility of the compounds to allow for the preparation of highly concentrated solutions.

For topical or nasal administration, penetrants appropriate to the particular barrier to be permeated are used in the formulation. Such penetrants are generally known in the art The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder that may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of the interleukin-1-related polypeptide 1, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example IL-1RP1 or fragments thereof, antibodies of IL-1RP1, agonists, antagonists or inhibitors of IL-1RP1, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between toxic and therapeutic effects is the therapeutic index, and it can be expressed as the ratio, LD50/ED50. Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors that may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc. Pharmaceutical formulations suitable for oral administration of proteins are described, e.g., in U.S. Pat. Nos. 5,008,114; 5,505,962; 5,641,515; 5,681,811; 5,700,486; 5,766,633; 5,792,451; 5,853,748; 5,972,387; 5,976,569; and 6,051,561.

The following Examples illustrate the present invention, without in any way limiting the scope thereof.

EXAMPLES

Example 1

Identification of a Novel Interleukin 1 Related Human DNA Sequence Using Bioinformatics Public and in-house databases are initially searched with the predicted amino acid sequences for human IL-1 beta (IL-1β) (Genbank Accession Number AAC03536) and a novel human IL-1 homolog 50795, later published as IL-1H1, (Genbank Accession Number AAF69248.1). TBlastN algorithm is used and the hits are aligned with ClustalW. One 229-nucleotide sequence is found to be unique within the in-house database. This sequence is then used to identify additional genomic sequences from the public and in-house databases (Genbank Accession number AF200492). A one 1 kb genomic sequence flanking the identified genomic fragment is translated into 6 reading frames and aligned with IL-1β and IL-1H1 amino acid sequence using ClustalW. Additional 127 nucleotides encoding a protein homologous to IL-1β and IL-1H1 is found 298 nucleotides upstream of the 5' end of the original genomic sequence.

Further analyses of isolated cDNA clones is done using ClustalW, BlastN, tBlastN according to conventional methods.

Example 2

Preparation of Full-length cDNA Encoding the Novel Interleukin-1 Related Polypeptide 1 Consisting of SEQ ID NO:1

Polymerase chain reaction (PCR) is used to isolate cDNA encoding the novel interleukin-1 related polypeptide (IL-1RP1). In all experiments AdvanTaq™ DNA polymerase (Clontech) is used. Two primers vio#3: 5'-GTC-CCCATTTTCCTGGGGATCCAGGG-3' (SEQ ID NO: 12) corresponding to predicted AA sequence VPIFLGIQG (SEQ ID NO: 13) and vio#4: 5'-ACCAGCTCTGTTCAAAG-TAAAACTTGG-3' (SEQ ID NO: 7) corresponding to predicted AA sequence RTKFYFEQSW (SEQ ID NO: 8) are synthesised (FIG. 1) and a two step PCR (95° C.—2 min.;

[95° C.—30 sec., 68° C.—1 min.]×35; 72° C.—3 min) is performed in the volume of 25 µl. Each reaction contains 1×Advantage 2 PCR buffer and dNTP mix (Clontech). A panel of Clontech Marathon-Ready™ double-stranded cDNA (3 µl per reaction) from a variety of human tissues is used as a source of template cDNA. Amplified 295 and 595 nt PCR products correspond to IL-1RP1 cDNA and genomic DNA, respectively. The 295 nt PCR product amplified from Clontech Marathon-Ready™ double-stranded cDNA from Fetal Human Intestine where IL-1RP cDNA is the most abundant, is purified using Gel Extraction Kit (Qiagen) and cloned into pCR-Blunt II-TOPO vector (Invitrogen, Carlsbad, Calif.) according to manufacturer supplied protocol. Plasmid DNA minipreps are prepared using Plasmid DNA Miniprep Kit (Qiagen) and sequenced in both strains with T7 and M13 reverse primers (ACGT lnc, Bethesda, Md.). A Clone (#6) is found to be free of PCR introduced mutations compared to human genomic sequence and is used to reconstruct a full-length cDNA.

A 5'RACE procedure is performed using two sets of primers: vio#4 and APi (Clontech); and vio#7: 5'-CTC-CAGCTGTAGGGAAGGCCCCTC-3', (SEQ ID NO: 7) corresponding to predicted AA sequence EEGPSLQLE (SEQ ID NO: 10) (FIG. 1) and AP2 according to protocol provided by the supplier. The first PCR is performed on Clontech Marathon-Ready™ double-stranded cDNA from Fetal Human Intestine using vio#4 and APi primers in three identical 25-µl reactions in a two step PCR (95° C.—2 min.; [95° C.—30 sec., 68° C.—3 min.]×35; 72° C.—3 min.). PCR mixes are pooled and extracted once with 75 µl of Phenol:Chloroform:lsoamyl alcohol—25:24:1 (Gibco BRL) and once with 75 µl of Chloroform:lsoamyl alcohol—24:1. Total PCR products are precipitated with equal volume of Isopropanol for 30 mm at–20C. Precipitated material is centrifuged at 13 000 rpm for 30 mm and the pellet is washed once with ice-cold 70% Ethanol and resuspended in 100 mls of TE buffer, 1×(Boehringer Mannheim, Ridgefield, Conn.). Second PCR is performed with vio#7 and AP2 primers using 2 µl of resuspended first PCR products as described. A major 360 nt PCR product is purified and cloned into pCR-Blunt II-TOPO vector (Invitrogen). Plasmid DNA minipreps are sequenced with T7 and M13 reverse primer. 5'RACE clone #4 is used to reconstruct the full-length cDNA.

To reconstruct IL-1RP1 full-length cDNA Clone#6 is cut with Bam HI and Xho I and 5'RACE Clone#4 is cut with Not I and Bam HI. Both cDNA fragments are purified and ligated into pFastBac (Gibco BRL, Rockville, Md.) vector pre-digested with Ho land Not I. Clones with correct IL-1RP cDNA are selected by BAM HI digest and the primary sequence is verified by sequencing with custom made primer #17A 5'-TAT AGT TCT AGT GGT TGG CT- 3' (SEQ ID NO: 11).

Figure 7:
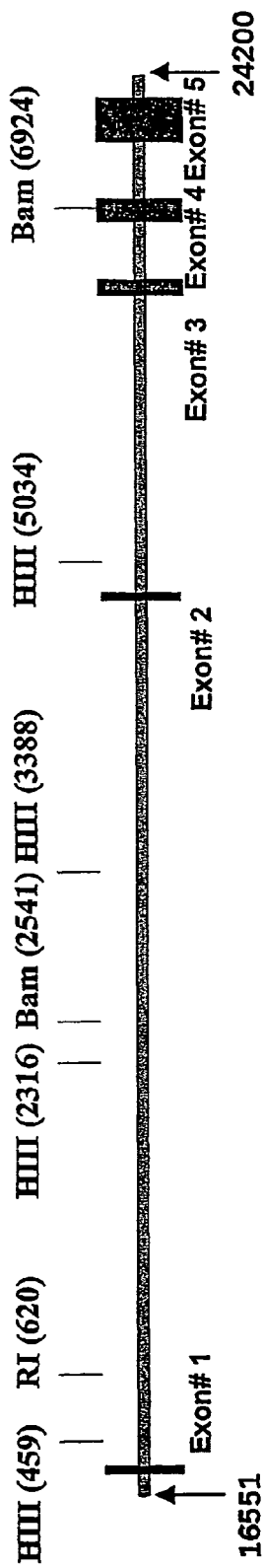
FIG. 7 depicts the exon/intron structure of human IL-1RP1.

Preparation of genomic DNA containing the IL-1RP1 gene can be accomplished by PCR using primers flanking the coding region according to conventional methods. Alternatively, a genomic library in lambda or P1 bacteriophage, BAC or plasmid libraries can be screened using PCR or hybridization technologies as known to one of skill in the art. As disclosed herein, information regarding the genomic sequence of the IL-1RP1 protein of the present invention is depicted in FIGS. 2 and 7 and is obtained by searching a public database, for example, the Human Genome database, according to conventional methods.

Example 3 mRNA Expression of IL-1RP1

To determine the relative abundance of IL-1RP1 in different human tissues, and hence its potential utility, an RT-PCR experiment (as described in Example 2) is carried out using a large panel of cDNAs derived from 24 different human tissue RNA. The panel is a premade panel obtained from OnGene (OnGene Inc., Rockville, Md.) wherein each cDNA is present in exact amounts. The equivalency of RNA amounts is verified by a control PCR carried out with primers to human beta-actin, a housekeeping gene present in roughly equal amounts in all tissues. Two primers for IL-1RP1, vio#3: 5'- GTCCCCATTTTCCTGGGGATC-CAGGG-3' (SEQ ID NO: 12) corresponding to predicted AA sequence VPIFLGIQ (SEQ ID NO: 13) and vio#4: 5'-ACCAGCTCTGTTCAAAGTAAAACTTGG-3' (SEQ ID NO: 7) corresponding to predicted AA sequence RTK-FYFEQSW (SEQ ID NO: 8) are synthesized and a two step PCR (95C—2'; [95C—30":68C—1']×35; 72C—3') is performed from the panel of 24 human tissues. The 295 nt PCR product is again cloned into pCR-Blunt II-TOPO vector (Invitrogen Inc., Carlsbad, Calif.) and sequenced to verify that it indeed corresponds to the IL-1RP1 gene. In addition, after PCR the products are analyzed by electrophoresis, blotted to a Nylon membrane (a Southern blot) and hybridized to a $P^{32}$ labeled probe derived from the IL-1RP1 cDNA described in Example 2. This blot is washed at high stringency (0.1×SSC 0.1% SDS for 1 hour) to ensure specific hybridization. The resulting hybridization signal is revealed by autoradiography using exposure to Kodak XAR-5 film. All the above procedures are performed using conventional methods.

As shown in FIG. 4, IL-1RP1 is present in low amounts in a variety of tissues. However, skin expressed very high levels of IL-1RP1 mRNA. This level is at least 10-fold higher than in other tissues. This high level of expression in skin indicates that IL-1RP1 may be of particular relevance to inflammation in the skin and is may be important in the regulation of diseases such as psoriasis and contact dermatitis.

What is claimed is:

1. An isolated polypeptide comprising the amino acid sequence set forth in SEQ ID NO:1.

2. An isolated polypeptide consisting of the amino acid sequence set forth in SEQ ID NO:1.

3. An isolated DNA molecule comprising a nucleic acid sequence that encodes the polypeptide of claim 1.

4. A vector molecule comprising the isolated DNA according to claim 3.

5. The vector molecule according to claim 4 comprising transcriptional control sequences.

6. An isolated host cell comprising the vector molecule according to claim 5.

7. The isolated DNA according to claim 3, comprising a nucleotide sequence selected from the group consisting of the nucleotide sequence set forth in SEQ ID NO:2 and the nucleotide sequence set forth in SEQ ID NO:3.

8. A vector molecule comprising an isolated DNA molecule according to claim 7.

9. The vector molecule according to claim 8 comprising transcriptional control sequences.

10. An isolated host cell comprising the vector molecule according to claim 9.

11. A host cell which can be propagated in vitro and which produces a polypeptide according to claim 1, wherein said cell comprises at least one transcriptional control sequence that is not a transcriptional control sequence of the natural endogeneous human gene encoding the polypeptide of claim 1, wherein said one or more transcriptional control sequences control transcription of a DNA encoding a polypeptide according to claim 1.

12. A method for producing a polypeptide as defined in claim 1, said method comprising culturing a host cell having incorporated therein an expression vector comprising an exogenously-derived polynucleotide encoding a polypeptide comprising the amino acid sequence as set forth in SEQ ID NO:1 under conditions sufficient for expression of the polypeptide in the host cell, thereby causing the production of the expressed polypeptide.

13. The method according to claim 12, said method further comprising recovering the polypeptide produced by said cell.

14. The method according to claim 12, wherein said exogenously-derived polynucleotide encodes the polypeptide consisting of the amino acid sequence set forth in SEQ ID NO:1.

15. The method according to claim 12, wherein said exogenously-derived polynucleotide comprises the nucleotide sequence as set forth in SEQ ID NO:2.

16. The method according to claim 12, wherein said exogenously-derived polynucleotide comprises the nucleotide sequence as set forth in SEQ ID NO:3.

17. The method according to claim 12, wherein said exogenously-derived polynucleotide consists of the nucleotide sequence as set forth in SEQ ID NO:3.

* * * * *

SEQUENCE LISTING

<160> NUMBER OF SEQ ID NOS: 11

<210> SEQ ID NO 1
<211> LENGTH: 152
<212> TYPE: PRT
<213> ORGANISM: Human

<400> SEQUENCE: 1

Met Cys Ser Leu Pro Met Ala Arg Tyr Tyr Ile Ile Lys Tyr Ala Asp

```
  1               5                  10                  15
Gln Lys Ala Leu Tyr Thr Arg Asp Gly Gln Leu Leu Val Gly Asp Pro
            20                  25                  30

Val Ala Asp Asn Cys Cys Ala Glu Lys Ile Cys Ile Leu Pro Asn Arg
            35                  40              45

Gly Leu Ala Arg Thr Lys Val Pro Ile Phe Leu Gly Ile Gln Gly Gly
            50                  55                  60

Ser Arg Cys Leu Ala Cys Val Glu Thr Glu Glu Gly Pro Ser Leu Gln
 65              70                  75                  80

Leu Glu Asp Val Asn Ile Glu Glu Leu Tyr Lys Gly Gly Glu Glu Ala
                85                  90                  95

Thr Arg Phe Thr Phe Phe Gln Ser Ser Gly Ser Ala Phe Arg Leu
                100                 105                 110

Glu Ala Ala Ala Trp Pro Gly Trp Phe Leu Cys Gly Pro Ala Glu Pro
            115                 120                 125

Gln Gln Pro Val Gln Leu Thr Lys Glu Ser Glu Pro Ser Ala Arg Thr
130                 135                 140

Lys Phe Tyr Phe Glu Gln Ser Trp
145                 150
```

<210> SEQ ID NO 2
<211> LENGTH: 534
<212> TYPE: DNA
<213> ORGANISM: Human

<400> SEQUENCE: 2

```
gatcagggtt ccaggaactc aggatctgca gtgaggacca gacaccactg attgcaggaa    60
tgtgttccct ccccatggca agatactaca taattaaata tgcagaccag aaggctctat   120
acacaagaga tggccagctg ctggtgggag atcctgttgc agacaactgc tgtgcagaga   180
agatctgcat acttcctaac agaggcttgg cccgcaccaa ggtccccatt ttcctgggga   240
tccaggagg gagccgctgc ctggcatgtg tggagacaga gaggggcct tccctacagc    300
tggaggatgt gaacattgag gaactgtaca aggtggtga agaggccaca cgcttcacct    360
tcttccagag cagctcaggc tccgccttca ggcttgaggc tgctgcctgg cctggctggt   420
tcctgtgtgg cccggcagag ccccagcagc cagtacagct caccaaggag agtgagccct   480
cagcccgtac caagttttac tttgaacaga gctggtaggg agacaggaaa ctgc         534
```

<210> SEQ ID NO 3
<211> LENGTH: 459
<212> TYPE: DNA
<213> ORGANISM: Human

<400> SEQUENCE: 3

```
atgtgttccc tccccatggc aagatactac ataattaaat atgcagacca gaaggctcta    60
tacacaagag atggccagct gctggtggga gatcctgttg cagacaactg ctgtgcagag   120
aagatctgca tacttcctaa cagaggcttg gcccgcacca aggtcccat ttcctgggg    180
atccaggag ggagccgctg cctggcatgt gtggagacag aagagggcc ttccctacag    240
ctggaggatg tgaacattga ggaactgtac aaggtggtg aagaggccac acgcttcacc    300
ttcttccaga gcagctcagg ctccgccttc aggcttgagg ctgctgcctg gcctggctgg   360
ttcctgtgtg gcccggcaga gccccagcag ccagtacagc tcaccaagga gagtgagccc   420
tcagcccgta ccaagttta ctttgaacag agctggtag                           459
```

-continued

```
<210> SEQ ID NO 4
<211> LENGTH: 7660
<212> TYPE: DNA
<213> ORGANISM: Human

<400> SEQUENCE: 4
atgcccaggc tcttcttcct tcatgtcctg cagccaatta tagagattgg tgcaggcctg      60
acccacctgt accagacggt ataaacacag cgcaatgccc tggagaaatc agttggagtc     120
tccagggatc agggttccag gaactcagga tctgcaggtc agtgatggac aggcaatatt     180
ctctctctct tttctttctt ttctactctc tcctgtcaat atctctggta tgccctctat     240
cccttcactc ctcctggcaa gctgtctagg taacaaggta gtcccctcat atgacatgat     300
gggacatcaa aaacatttag gagcacataa agagatttga ggagaaggaa taggttaagc     360
caaatcaaga tttctgaact acttagaaca actgacttta gaaagtaatc tcaaaagaaa     420
ccatctgggc caatggtatt caaaccgtgt ttggtggaag cttaagagat tttttgtttt     480
cgttttttt tttttgtgc tccttggtag ctcctcagtg tcttctttgt aggcaagaga     540
aatactagca gggttccaaa gtctccattg cttcctgtgt cagcaaagca gctgcccttt     600
atcctttta caatcattag aattctgcat aaaattttat tgtgaaactt aaaacagttt     660
tgaaagatac cttactcaat cttccatcc aatgttgata agttgaaggc ccagggataa     720
aaggtggcaa ataaattgg tagcagagct aggtctagga ctcagccttt ctattcaaag     780
tctgctctgt gtgttctat gtcctggcca caaggaccag ggtagttcaa ttagggtggt     840
tggagagagc ttcaagtgag ctgtaagcca tgcttcatga cttcaagatc ttataaactt     900
ttataaggga acaaatatc tttatgtaca acaataaata atacagtaaa atttaatagg     960
agttcagagt agagttacaa tagtaaggga aagattcatt aaactctgag tcatggaatt    1020
ataaatagtt tggcctagaa agaaccttca taaccacata atctaatccc atgaatgtat    1080
agtgctgaaa ctgagggttg gaggttaaaa gacataaccc tgtatgtcta agctgtaact    1140
ctacactggt aattaatttg atagaactag atactgaacc catctatact gatactatct    1200
ccagtgatct taatatcaaa agatctgaat ggatgacaat gagaagggat gacttttgag    1260
gcagggagaa caatgggaca cctgtgagta cgtccactga aagataaga aaggaattat    1320
gtcgccagga ggtgtggttt agtgtccatg agaagtgag atgctatcac acaagaaaat    1380
cagtgccaga cggtgacaaa acagtcagtc actgtagatt ctagagctgg gcagggatgt    1440
ggtgaaaaa atctttagaa cgtgggtcca cattcctcac ataggttgga atgaatgaaa    1500
ggcagaaaaa ccgggaatac aagtacagta gtaatggcaa ttaaaaacac aaagttatat    1560
tttaaagaaa taacctgtag ggacttgata agttagacac tgagtcagga gaagtaggag    1620
atattgtcaa tgagtctcag gttttgaata tcactggtga gaggaatatt atgacagtga    1680
gagaaatgaa attgggagga atgtgtgggc tgggaggaga agataattaa cttaaccta     1740
aatatatttg gttggatatc agcaggatgt ccaaagtggg ctgtcctgta ggctgcagga    1800
ggtaaagtgg gatgtgcagt ctacatttgg gagccattag cccaagataa tcattgcagc    1860
tgtagaagtc aatgaattgc agcttaatat gatgtgaaat agaagtgctt aggaccttgt    1920
tagccttagg ggtggcccca gaaggaggtg aaatctacag tggagaaag aggtgtgaag    1980
ggagtcattc aatgtcaagg gttccaagga ggcaatgact aaatatcaaa ggaatcaaaa    2040
gaatctctgg atcttgctcc acagaagtta atattggtct tggacagaac atcccacata    2100
gatactgtgc aggagaatga tgaaggatag gacagggtgc tgtgcaaaag aacatgggga    2160
```

```
aagcccaagt tagctgatg gcagtgtttg agccaggaca ggtgaattgc ggaggtctga    2220
gagccagatg ccatgtccag ggagaaatga gaggaagaaa agagggatat agactgaagt    2280
tcagtgaaaa gtcatttgag gaaaataggg aggggaagct ttgggggtga ggcatgtggc    2340
acactgggag gggcttggca cacagcagag gttcagcacc aagacccagg ctctctgatg    2400
gaccagacgc tagcttccta cccttactca cttcatcaca atctatcaga acccaggcgg    2460
agggagccga ataggggagc cttttgggaaa gacactgtac atttttggctg tgccagaatg    2520 ggaggtttct agggcccatg ggatccagct ggactggacc agcattgaat tcttccagc    2580 tctttgagct gacactgacc cagagtggga gtcatcagct tgctatccac cttcacccag    2640
ggccctccac tttgttgccc cacctagatc tgggcacagc taccacactg cccactgtcc    2700
tgctgctaca accaaagaag ccccagtggt ttggccaagg ggagcccatc atcaagtggg    2760
cttgcattga ggccatgatg ctgttgagtt atctgtactg ggggattgtc tagtcctta    2820 ggactcaaag tgctggccag gaggaaccag cagcattgac atcacctggt tgcatatttg    2880
aaatgtacag tctcaggccc caccccaggc ctgaaaaacc agaatctgtt atttttaacaa    2940 gaactgcagg tggtttatat atttattaat aagtgtgaag aatggaatga aagtacacca    3000
gttcccaagc agcatggctg attgctgaa tcactccaag tcctactgaa ttagaaccttt    3060 cggcccagga aatagtaatt atacagagtc ccccaggtga tgcagatggg caggcacatt    3120
taggagccaa tgactttaac tgaacacttc atttaaaaaa tgttgaaact tacttgatac    3180
tacaaaggaa attcatgttc attataggaa aatgttgata tgtttaaaaa attactcata    3240 aagcccatagg taagtggtgc aacaacacga gtaacatttc tatgtatgtg tctctatgtg    3300
tggatttaaa tagaattaca gtgtacactt gatttataat ctgcattttt cacctaatat    3360
attttgaaaa tttttatgtc ctaaaacaag cttctataat atcatcttta acaaacacat    3420
acatccttat ttattgaatt ttgctataat ttccttagcca attacctatt actgaaaatt    3480 cagattttt tcaacttctt gctattgtaa aaaattatgc agtgaacatt tttgtaagta    3540
aacatttggg caatccgtta ttttttcctaa gagtaaggga aacacatgca atcacaaagt    3600
atacagaatg ctttaagact ttcattcaca gcaccaacat cccctccagaa tttgcacttg    3660 ttagtcccta ttatccttca ctctaagtct caaagtcata ccccaaggcc tggggacaga    3720
aaatgacttg tccaaagtga cagtgacaga cccagtacta aaagccacct tggctacagc    3780 cctgttctg gaacttgaga gctgaggtgg ttggaagccg tatcctcagc acccacctgt    3840
tccttctcac ctgcctcccc agggtccctc agcatctctc tattcctccc tgagccctat    3900
tactttcttc cacctgcctt cttcctttct cttctctcat tttctgcttt cttatatttt    3960
ttcttctcta ttcccttctt atttggtgag aatcagatct actcggtaaa cctcagccct    4020
agtcatactt gcgttacttt cctgagctaa tttccaactc ctgattagct ctgggtttat    4080
ttccatgcta aattctggac tggcctttcc aatgggtgtt catttttaggg aagagctcta    4140 ggacaggata acccatcggg aaggagcaga gtcatgtgag gctgtgtggc ctggcattta    4200
tacagggcca ctatcttcac tgtgccattt tccatctgga acagaatggg ggagtttgga    4260
tgggctgttt tcggcagtct tggccaagca cttctagtca ctaggaatga tgttttccaa    4320
ctctctgggg agacccacc agcctcactg ctgctggaga cccttctag ttgtgctctc    4380 ttctttcact ctgggctcta gttatctaac ccttggctag ttatggggc ggggtgtgg    4440 tgccctgttg gccaacaggg cagtgggact gggtttgagc tgggcttatc ctccaactgt    4500
```

```
gagggaggct acagcacact ccaccccact ctcagggctg ggaattgttg tggctcagct    4560
atttggggga atctgttttc cagtttctca gaaccagcgc aagcacacac atcccaggct    4620
cacacccctg gtggctggac ttgctcccgg atagcctcag tcagggagag gcagagctgc    4680
ctggagcctg ctgggctggt ggaagccttg gtggattctg gcaggccaat tatagacgaa    4740
tggcctgggg aacccgtgca gcccttggct gagtggttct aagccccagc acgtctgcct    4800
ctggcttcac ccagcctcct tttctaactg cccttctctc ctccccatca gtgaggacca    4860
gacaccactg attgcaggaa tgtgttccct ccccatggca agatactaca tgtaagttgt    4920
cctggcatgt ccctgctttc caagccaggg ggtcagggtg ggaagaggaa aggaatgctg    4980
agtcagagga tgaggctcct tctcacctta gaaattgcaa gtgccccata attaagcttc    5040
atcatcacca cagtagcaac agctctttcc tgaacgtctg caagatgcca gccaatctac    5100
tgcctcatct ctgttccaaa aagtctgtaa gtggagtgtt attaaaccca ttttacagat    5160
ctggaagctg aggctcaaag agggtaaata acttccccca tgtcacacag ctaccaaaag    5220
gcagagccag gaatcagact tcatgtcctc tgtgctgctc catccgcctc tctgaaatgt    5280
cagaaagttt tgaatctcaa tgacagcatc ttgatggtgg tccctgtggc ctttactccc    5340
agtgtgggct tctaacactt acttacattt catctcattt gagatttgca tccttcctta    5400
tcttttacta ctttgttgtc tgtgattttg tcataagctc ctttcaggaa ggaggtgagg    5460
cataagaaaa atcaaagagg actctgggat gcatttcctc tgcccctccc atggaccctg    5520
taatgtccag ggctgtgtcc tggacaaggt gggtggggag cagtcctggt ctcaaggagg    5580
tgacagcctg gctgggaagc aagacacata cataggaagc acataaatga caaagcagat    5640
gtcagcactt cagggcatct aatctgggtt ctggtctcca aatagaatgc tgctggcatg    5700
tgagttgtca catctgggtt gtcaaggtgg caaggggaat gccagataac acgcccagga    5760
tctttccgga agtttatttt tattgtacaa gtgaacctgc tttaaatatg tacagtcatt    5820
agctaagggt attatcgtta gctgttattg agatagaaaa atcccctgga ggtggtggaa    5880
tttgtccaga ggttctgccc taaaaggtta atgagagctc tccagccctg acagcagctg    5940
acaggcatct ttgaaaccaa ctaggtgact gagctaatac cctgcatgac tttgaagcct    6000 ttaaatatc tgaaaagcaa atcacacttc agtatacact caatctctgt actaaagaga    6060
ataacatttt ataaacaatt agggcaggcc caaaaaattt aagataaggt ccactgtatc    6120
ccaaagtcat ctgagcctca ctaagaaatt tctcaggaag ccaggaacat tttcttfacc    6180 cctctgtcag agggcattgg ctctccgttc tcctctgaag gcctccccaa gccatgagaa    6240
ggcaggaagc acagcctctg aaaagcaaga acacaggaga ccttccttgc tttaaggctg    6300
gcctggtctt tacctgctct tgggagtgac cattcccctc ttaccacctg tgaaggagag    6360
aaaatcgccc aaatgctcaa ggtggtgatt cagagcatgg aagtggaagg gcttgggggc    6420
cagtggtgca taagggaat gggccatcag cactgtcata ctgtttcaga attaaatatg    6480
cagaccagaa ggctctatac acaagagatg gccagctgct ggtgggagat cctgttgcag    6540
acaactgctg tgcaggtgag cttctggggc ctccacccca tgctccatct gccataggcc    6600
ctcccttctc ttcttccctt tcctccccag cagggtca gcagctgccc ccagtgacag    6660
tgagaagggc cagagagcag ctgtggcctc tcctagcgag gggacatgac tcctgcagaa    6720
gtcctggctc accgtccagt ctgcatgcag ggccaggcca ggtgtgccca tgtccagttc    6780
cttcctgcct gagcctttac ctgccaagag cctgcaacat ggggttccct tgtcccttga    6840
ctcttctctc tcttccctcc tagagaagat ctgcatactt cctaacagag gcttggcccg    6900
```

-continued

```
caccaaggtc cccatttcc tggggatcca gggagggagc cgctgcctgg catgtgtgga      6960
gacagaagag gggccttccc tacagctgga ggtgagaggc ctctccccat tctaggggac      7020
actgcagacc tggcctgacc cctgggatgc tctggcatct tgtgcctat ctgtggattc       7080 ccagccaggt ccacatgtcc tacttcctca ggtttccacc atctccctct gcacctagca      7140
ccaagaccct tgccctctag aatctgcaga aggcagtccc ttgggtaaaa accagccctg      7200
tcaggtcctt ttttggccaa gccccagagg cctccagggc taacacctcc atcagcactc      7260
tcattctgca gccatccacc ttgcccccac aggatgtgaa cattgaggaa ctgtacaaag      7320
gtggtgaaga ggccacacgc ttccacttct tccagagcag ctcaggctcc gccttcaggc      7380
ttgaggctgc tgcctggcct ggctggttcc tgtgtggccc ggcagagccc cagcagccag      7440
tacagctcac caaggagagt gagccctcag cccgtaccaa gttttacttt gaacagagct      7500
ggtagggaga caggaaactg cgttttagcc ttgtgccccc aaaccaagct catcctgctc      7560
agggtctatg gtaggcagaa taatgtcccc cgaaatatgt ccacatccta atcccaagat      7620
ctgtgcatat gttaccatac atgtccaaag aggttttgca                           7660
```

<210> SEQ ID NO 5
<220> FEATURE:
<223> OTHER INFORMATION: primer

<400> SEQUENCE: 5

000

<210> SEQ ID NO 6
<211> LENGTH: 9
<212> TYPE: PRT
<213> ORGANISM: Artificial Sequence
<220> FEATURE:
<223> OTHER INFORMATION: predicted amino acid sequence, chemically
      synthesized

<400> SEQUENCE: 6

Val Pro Ile Phe Leu Gly Ile Gln Gly
 1               5

<210> SEQ ID NO 7
<211> LENGTH: 27
<212> TYPE: DNA
<213> ORGANISM: Artificial Sequence
<220> FEATURE:
<223> OTHER INFORMATION: primer

<400> SEQUENCE: 7
accagctctg ttcaaagtaa aacttgg                                          27

<210> SEQ ID NO 8
<211> LENGTH: 10
<212> TYPE: PRT
<213> ORGANISM: Artificial Sequence
<220> FEATURE:
<223> OTHER INFORMATION: predicted amino acid sequence, chemically
      synthesized

<400> SEQUENCE: 8

Arg Thr Lys Phe Tyr Phe Glu Gln Ser Trp
 1               5                  10

<210> SEQ ID NO 9
<211> LENGTH: 24

-continued

```
<212> TYPE: DNA
<213> ORGANISM: Artificial Sequence
<220> FEATURE:
<223> OTHER INFORMATION: primer

<400> SEQUENCE: 9
ctccagctgt agggaaggcc cctc                                          24

<210> SEQ ID NO 10
<211> LENGTH: 9
<212> TYPE: PRT
<213> ORGANISM: Artificial Sequence
<220> FEATURE:
<223> OTHER INFORMATION: predicted amino acid sequence, chemically
      synthesized

<400> SEQUENCE: 10

Glu Glu Gly Pro Ser Leu Gln Leu Glu
 1               5

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tatagttcta gtggttggct                                               20
```